(12) United States Patent
Nicolaou et al.

(10) Patent No.: US 7,410,998 B2
(45) Date of Patent: Aug. 12, 2008

(54) INHIBITORS OF NADH:UBIQUINONE OXIDOREDUCTASE

(75) Inventors: Kyriacos C. Nicolaou, La Jolla, CA (US); Jeffrey Pfefferkorn, Kalamazoo, MI (US); Guo-Qiang Cao, Thousand Oaks, CA (US); Anthony Roecker, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 410 days.

(21) Appl. No.: 10/363,181

(22) PCT Filed: Sep. 6, 2001

(86) PCT No.: PCT/US01/28104

§ 371 (c)(1),
(2), (4) Date: Jul. 23, 2003

(87) PCT Pub. No.: WO02/20008

PCT Pub. Date: Mar. 14, 2002

(65) Prior Publication Data

US 2004/0034239 A1 Feb. 19, 2004

Related U.S. Application Data

(60) Provisional application No. 60/230,630, filed on Sep. 6, 2000.

(51) Int. Cl.
*A61K 31/35* (2006.01)
*C07D 311/00* (2006.01)

(52) U.S. Cl. .................. 514/451; 549/405; 549/407; 549/408

(58) Field of Classification Search .............. 514/456; 549/405, 407, 408
See application file for complete search history.

(56) References Cited

OTHER PUBLICATIONS

Kumar, J. K. et al 'Further dihydrochalcones from *Crotolaria ramosissima*' CA 132:105317 (1999).*
Nicolaou K.C. et al 'Natural Product-like Combinatorial Libraries Based on Privileged Structures. 3. The "Libraries from Libraries" Principle for Diversity Enhancement ofBenzopyran Libraries' CA 134:17372 (2000).*
Jain, AC et al 'Synthesis of erthrinin-A and related isoflavones' CA 104:5664 (1986).*
Nicolaou et al Combinatorial synthesis of novel and potent inhibitors of NADH:ubiquinone oxidoreductase CA 134:260863 (2001).*
Nicolaou et al Natural product-like combinatorial libraries based on privileged structures. 3. the libraries from libraries principle for diversity enhancement of benzopyran libraries CA 134:17372 (2000.*
Kumar et al Further dihyrochalcones from *Crotolaria ramosissima* A 132:105317 (1999).*
Villain et al An easy synthesis of angular 6",6"-dimethylpyanoisoflavones CA 87:39333 (1977).*
Adityachaudhury et al Synthesis of tetrahydroflemichapparin A CA 82:170595 (1975).*
Jain et al Nuclear prenylation of 2,4-dihydroxyphenylbenzyl ketone. Synthesis of linear and angular 6",6"-dimethylpyranoisoflavones, and their 2-methyl and 2-phenyl analogs CA 76:99452 (1972).*

(Continued)

*Primary Examiner*—Janet L. Andres
*Assistant Examiner*—Raymond Covington
(74) *Attorney, Agent, or Firm*—Thomas Fitting; Donald G. Lewis

(57) ABSTRACT

Benzopyran-based inhibitors of NADH:ubiquinone oxidoreductase for inhibiting the growth of cancer cells.

7 Claims, 19 Drawing Sheets

OTHER PUBLICATIONS

Zelinski et al Acetylenic reactions of 2-(phenylethynyl)tetrahydropyran CA 53:7016 (1959).*

Hashimoto, et al CA 117:69734 (1992).*

Tanaka, et al CA 106:47187 (1987).*

Nicolaou et al CA 134:260863 (2001).*

Hashimoto CA 117:48593.*

Earley, et al., "Photolabelling of a mitochondrially encoded subunit of NADH dehydrogenase with [$^3$H]dihydrorotenone", *FEBS Lett.* 219: 108-113 (1987).

Crombie, et al., "The Rotenoid Core Structure: Modifications to Define the Requirements of the Toxophore", *Bioorg. Med. Chem. Lett.* 2: 13-16 (1992).

Levett, et al., "Structural Requirements for Respiratory Inhibition by Rotenoids: Is an Intact B/C Ring System Essential?", *Bioorg. Med. Chem. Lett.* 4: 505-508 (1994).

Gerhäuser, et al., "Rotenoids mediate potent cancer chemopreventive activity through transcriptional regulation of ornithine decarboxylase", *Nature Med.* 1: 260-266 (1995).

Ding, C. Z., "A Convenient Synthesis of 6-Substituted-2,2-dimethyl-2H-1-Benzopyrans", *Syn. Commun.* 26: 4267-4273 (1996).

Udeani, et al., "Cancer Chemopreventive Activity Mediated by Deguelin, a Naturally Occurring Rotenoid", *Cancer Res.* 57: 3424-3428 (1997).

Gerhäuser, et al., "Regulation of Ornithine Decarboxylase Induction by Deguelin, a Natural Product Cancer Chemopreventive Agent", *Cancer Res.* 57: 3429-3435 (1997).

Fang, et al., "Anomalous Structure-Activity Relationships of 13-homo-13-Oxarotenoids and 13-homo-13-Oxadehydrorotenoids", *Chem. Res. Toxicol.* 10: 853-858 (1997).

Nicolaou, et al., "Polymer-supported selenium reagents for organic synthesis", *Chem. Commun.*: 1947-1948 (1998).

Fang, et al., "Anticancer action of cubé insecticide: Correlation for rotenoid constituents between inhibition of NADH:ubiquinone oxidoreductase and induced ornithine decarboxylase activities", *Proc. Natl. Acad. Sci. USA* 95: 3380-3384 (1998).

Esposti, M. D., "Inhibitors of NADH-ubiquinone reductase: an overview", *Biochim. Biophys. Acta* 1364: 222-235 (1998).

Lümmen, P., "Complex I inhibitors as insecticides and acaricides", *Biochim. Biophys. Acta* 1364: 287-296 (1998).

Fang, et al., "New Bioactive Flavonoids and Stilbenes in Cubé Resin Insecticide", *J. Nat. Prod.* 62: 205-210 (1999).

Barrientos, et al., "Titrating the Effects of Mitochondrial Complex I Impairment in the Cell Physiology", *J. Biol. Chem.* 274: 16188-16197 (1999).

Nicolaou, et al., "Selenium-Based Solid-Phase Synthesis of Benzopyrans I: Application to Combinatorial Synthesis of Natural Products", *Angew. Chem. Int. Ed.* 39: 734-739 (2000).

Nicolaou, et al., "Selenium-Based Solid-Phase Synthesis of Benzopyrans II: Applications to Combinatorial Synthesis of Medicinally Relevant Small Organic Molecules", *Angew. Chem. Int. Ed.* 39: 739-743 (2000).

Nicolaou, et al., "Natural Product-like Combinatorial Libraries Based on Privileged Structures. 1. General Principles and Solid Phase Synthesis of Benzopyrans", *J. Am. Chem. Soc.* 122: 9939-9953 (2000).

Nicolaou, et al., "Natural Product-like Combinatorial Libraries Based on Privileged Structures. 2. Construction of a 10000-Membered Benzopyran Library by Direct Split-and-Pool Chemistry Using NanoKans and Optical Encoding", *J. Am. Chem. Soc.* 122: 9954-9967 (2000).

Nicolaou, et al., "Natural Product-like Combinatorial Libraries Based on Privileged Structures. 3. The "Libraries from Libraries" Principle for Diversity Enhancement of Benzopyran Libraries", *J. Am. Chem. Soc.* 122: 9968-9976 (2000).

Hashimoto, et al., "Preparation of benzopyran derivatives having antihypertensive and vasodilatory activity", Database Registry File on STN (Columbus, OH, USA), No. 117:69734, abstract, (see compound with RN 142314-64-5, 1992.

Hashimoto, et al., "Preparation of benzopyran derivatives as cardiovascular agents", Database Registry File on STN (Columbus, OH, USA), No. 117:48593, abstract, (see compound with RN 139081-48-4, 1991.

Tanaka, et al., "Chemical and chemotaxonomic studis of pterophytens. Chemical studies on the constituents of *Sceptridium ternatum* var. *ternatum*", Database Registry File on STN (Columbus, OH, USA), No. 106:47187, abstract, (see compound with RN 106235-42-1, 1986.

* cited by examiner

57: >3000 nM, Sch. 2

64: >3000 nM, Ref. 17

71: 730 nM, Sch. 2

58: >3000, Sch. 2

65: >3000 nM, Ref. 17

72: >3000 nM, Sch. 4

59: 2200 nM, Ref. 21

66: >3000 nM, Ref. 17

73: 2300 nM, Ref. 17

60: 1900 nM, Ref. 17

67: 470 nM, Sch. 3

74: 530 nM, Sch. 3

61: >3000 nM, Ref. 17

68: 1400 nM, Sch. 2

75: 160 nM, Sch. 3

62: >3000 nM, Ref. 21

69: 730 nM, Sch. 2

76: 340 nM, Sch. 3

63: >3000 nM, Sch. 3

70: 550 nM, Sch. 3

| Bridge | IC$_{50}$ (nM) | Bridge | IC$_{50}$ (nM) |
|---|---|---|---|
| Chalcone | 850 - (>3000) | Alkyne | 2300 |
| Stilbene | 2200 - (>3000) | Ester | 55 - (>3000) |
| Coumarin | 1900 - (>3000) | Amide | 2300 - (>3000) |
| Heterocycle | 1100 - (>3000) | Ether | 160 - 800 |

First Generation Lead Compounds:

|    | R   | IC$_{50}$ (nM) |
|----|-----|----------------|
| 42 | H   | 220            |
| 55 | OMe | 55             |

Strategic Regions for SAR Optimization

I   II   III   IV

Only moderate influence on activity.
$R^4$ = OH provided increased activity (relative to $R^4$ = H) while $R^3/R^4$ = Cl, OMe, $NO_2$ resulted in modest decreases in inhibitory activity.

Substituent pattern very important for activity.
optimal activity is observed for $R^5,R^6,R^7$ = OMe and for $R^5,R^6$ = OMe, $R^7$ = Br cases. Four fold less activity for $R^5,R^6$ = OMe only. All other patterns resulted in significant activity loss.

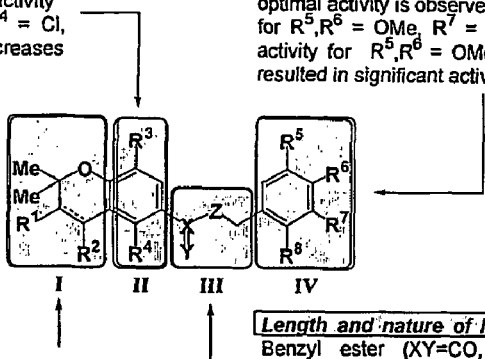

I  II  III  IV

Lipophilicity important for activity.
Olefin ($R^1$, $R^2$ = H) or saturated ring optimal for activity. Introduction of polar groups not well tolerated.

Length and nature of linkage crucial for activity.
Benzyl ester (XY=CO, Z=O), ketone (XY=CO), thioether (X=S), and styrene (XY=$CH_2$) afford optimal activities. Ethers and alkyl bridges are slightly less active whereas amides, thioamides, thioesters, thioketones, oximes, sulfonates, and sulfones are not tolerated.

Regions II and IV SAR Data

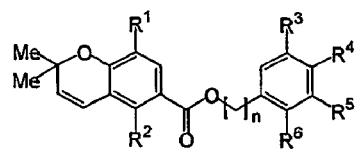

| | n | $R^1$ | $R^2$ | $R^3$ | $R^4$ | $R^5$ | $R^6$ | $IC_{50}$ (nM) |
|---|---|---|---|---|---|---|---|---|
| 91 | 1 | H | H | H | H | H | H | 1700 |
| 92 | 1 | H | H | H | Me | H | H | 1000 |
| 93 | 1 | H | H | H | Et | H | H | 720 |
| 94 | 1 | H | H | H | n-Bu | H | H | 1100 |
| 95 | 1 | H | H | H | $CF_3$ | H | H | 580 |
| 96 | 1 | H | H | H | H | H | OMe | 1230 |
| 97 | 1 | H | H | H | H | OMe | H | 900 |
| 98 | 1 | H | H | H | OMe | H | H | 830 |
| 99 | 1 | H | H | H | H | OMe | OMe | 530 |
| 100 | 1 | H | H | H | OMe | H | OMe | 1000 |
| 101 | 1 | H | H | OMe | H | H | OMe | 1800 |
| 102 | 1 | H | H | OMe | H | OMe | H | 770 |
| 42 | 1 | H | H | H | OMe | OMe | H | 220 |
| 103 | 1 | OMe | H | H | OMe | OMe | H | 2000 |
| 104 | 1 | Cl | H | H | OMe | OMe | H | 250 |
| 105 | 1 | $NO_2$ | H | H | OMe | OMe | H | 450 |
| 106 | 2 | H | H | H | OMe | OMe | H | 930 |
| 107 | 3 | H | H | H | OMe | OMe | H | 600 |
| 108 | 1 | H | H | H | OMe | OMe | OMe | 330 |
| 109 | 1 | H | H | H | OMe | OMe | H | OMe | 300 |
| 55 | 1 | H | H | OMe | OMe | OMe | H | 55 |
| 110 | 1 | H | OH | OMe | OMe | OMe | H | 44 |
| 111 | 1 | OMe | H | OMe | OMe | OMe | H | 820 |
| 112 | 1 | Cl | H | OMe | OMe | OMe | H | 95 |
| 113 | 1 | $NO_2$ | H | OMe | OMe | OMe | H | 190 |
| 114 | 1 | H | H | H | -OCH$_2$O- | | H | 650 |
| 115 | 1 | H | H | H | OEt | OEt | H | 540 |
| 116 | 1 | H | H | H | OEt | OMe | H | 260 |
| 117 | 1 | H | H | OEt | OEt | OEt | H | 950 |
| 118 | 1 | H | H | H | OMe | OEt | OMe | H | 69 |
| 119 | 1 | H | H | H | OMe | OMe | Br | H | 115 |
| 120 | 1 | H | H | H | OMe | OMe | H | Br | 49 |
| 121 | 1 | H | H | H | H | OBn | OMe | H | 330 |
| 122 | 1 | H | H | OMe | OBn | OMe | H | 86 |
| 123 | 1 | H | H | H | F | H | H | 1180 |
| 124 | 1 | H | H | H | F | F | H | 1230 |
| 125 | 1 | H | H | H | Cl | H | H | 900 |
| 126 | 1 | H | H | H | Cl | Cl | H | 590 |
| 127 | 1 | H | H | H | Br | H | H | 720 |

Figure 15B

| Cancer Cell Type | GI$_{50}$ (nM) | | | | Average[b] |
|---|---|---|---|---|---|
| | 165 | 158 | 178 | 55 | |
| Leukemia | | | | | |
| HL-60 | 340 | 14 | 840 | 1810 | 750 |
| K-562 | 730 | 1540 | 5090 | 2900 | 2800 |
| MOLT-4 | 96 | 340 | 1230 | 6800 | 2560 |
| RPMI-8226 | 940 | 3040 | 2660 | 4760 | 2850 |
| NSC Lung | | | | | |
| EKVX | 66 | 680 | 3930 | 8620 | 3320 |
| HOP-62 | 830 | 280 | 6690 | 31300 | 9780 |
| NCI-H226 | 330 | 1090 | 5560 | 15500 | 5620 |
| NCI-H322M | 180 | 560 | 2210 | 49600 | 13100 |
| Colon | | | | | |
| HCT-116 | 740 | 1370 | 4850 | 7930 | 3720 |
| HCT-15 | 440 | 12600 | 3970 | 8940 | 6490 |
| SW-620 | 660 | 23300 | 6400 | 21300 | 12900 |
| CNS | | | | | |
| SF-295 | 690 | 23100 | 4580 | 23300 | 12900 |
| SNB-19 | 660 | 17100 | 6110 | 11700 | 8890 |
| U-251 | 210 | 430 | 2580 | 14300 | 4380 |
| Melanoma | | | | | |
| LOX IMVI | 180 | 19700 | 3050 | 9100 | 8010 |
| MALME-3M | 320 | 13400 | 2370 | 7700 | 5950 |
| SK-MEL-5 | 490 | 1910 | 5160 | 3200 | 2690 |
| UACC-257 | 210 | 780 | 3010 | 14500 | 4630 |
| Breast | | | | | |
| MCF-7 | 3080 | 880 | 6570 | 9100 | 4910 |
| NCI/ADR-RES | 670 | 2500 | 2350 | 6800 | 3080 |
| HS 578T | 600 | 860 | 7400 | 25000 | 8470 |
| MDA-MB-435 | 2790 | 37200 | 7110 | 14800 | 15500 |
| Average[c] | 690 | 7380 | 4300 | 13600 | |

[a]Assays were performed by the Developmental Therapeutics Program of the National Cancer Institute, USA. The compounds were provided as DMSO solutions and evaluated for their *in vitro* cytostatic properties against 60 human cell lines using the NCI standard protocol. [b]Average GI$_{50}$ value for compounds 55, 158, 165 and 178 in a particular cell line. [c]Average GI$_{50}$ value for a single compound in all cell lines.

Figure 17

INHIBITORS OF NADH:UBIQUINONE OXIDOREDUCTASE

DESCRIPTION

1. Technical Field

The invention relates to inhibitors of NADH:ubiquinone oxidoreductase. More particularly, the invention relates to benzopyran-based inhibitors of NADH:ubiquinone oxidoreductase and to their use.

2. Background

NADH:ubiquinone oxidoreductase (Complex I, FIG. 1) is the first of three large enzyme complexes located in the cell's inner mitochondrial membrane which form the electron transport chain that carries electrons from NADH to molecular oxygen during oxidative phosphorylation. A variety of natural and synthetic inhibitors of Complex I (see representative examples in FIG. 2) have found multiple applications (Degli Esposti, M. *Biochim. Biophys. Acta* 1998, 1364, 222-235). There is significant interest in developing small molecule inhibitors of this enzyme for use as biological probes, insecticides, and potential chemopreventive/chemotherapeutic agents. Herein, the application of novel natural product-like libraries is disclosed for the discovery of a family of potent benzopyran-based inhibitors.

SUMMARY

The synthetic combinatorial libraries, modeled after natural products, were utilized to discover novel and structurally simple bioactive compounds as inhibitors of the enzyme NADH:ubiquinone oxidoreductase. The lead inhibitors were then optimized through the synthesis of focused libraries which refined specific sub-units of the lead compounds. Ultimately a collection of benzopyran-based inhibitors with $IC_{50}$ values 18-55 nM were identified. Several of these inhibitors were then evaluated in cell-based assays to evaluate their cytotoxic and cytostatic properties. Interestingly, while most of the compounds were relatively non-cytotoxic, several exhibit potent cytostatic activities across a variety of cancer types and cell lines. The ability of these small molecules to inhibit cancer cell growth, perhaps mediated by the ability to interrupt ornithine decarboxylase (ODC) activity, makes them potent chemopreventive/chemotherapeutic agents.

The first aspect of the invention is directed to a compound represented by the following structure:

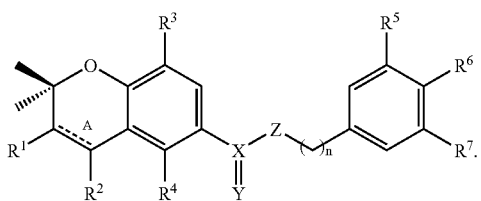

In the above structure, A is a π-bond that is either present or absent. $R^1$ and $R^2$ are radicals independently selected from —H, —F, —Cl, and —Br. $R^3$ and $R^4$ are radicals independently selected from —H, and —OH. $R^5$, $R^6$ and $R^7$ are radicals independently selected from —H, —OMe, —F, —Cl, and —Br. Z is a diradical selected from —(CH$_2$)— and —O—. X is selected from carbon and sulfur. Y is either absent or is a diradical or pair of radicals selected =O, =S, =CH$_2$, =CF$_2$, =NOH, =NOMe, =NOBn and (—H, —H). n is either 0 or 1. However, the following provisos apply: If X is sulfur, then Y is absent; if n is 0, then Z is —(CH$_2$)—; and if $R_4$ is —OH and Y is =O, then Z is —O— or —S—.

A second aspect of the invention is directed to the same compound as the first aspect of the invention, except Y can not be =O.

A third aspect of the invention is directed to the same compound as the first aspect of the invention, except $R^4$ can not be —OH. Preferred species of the first and third aspects of the invention are represented by the following structures:

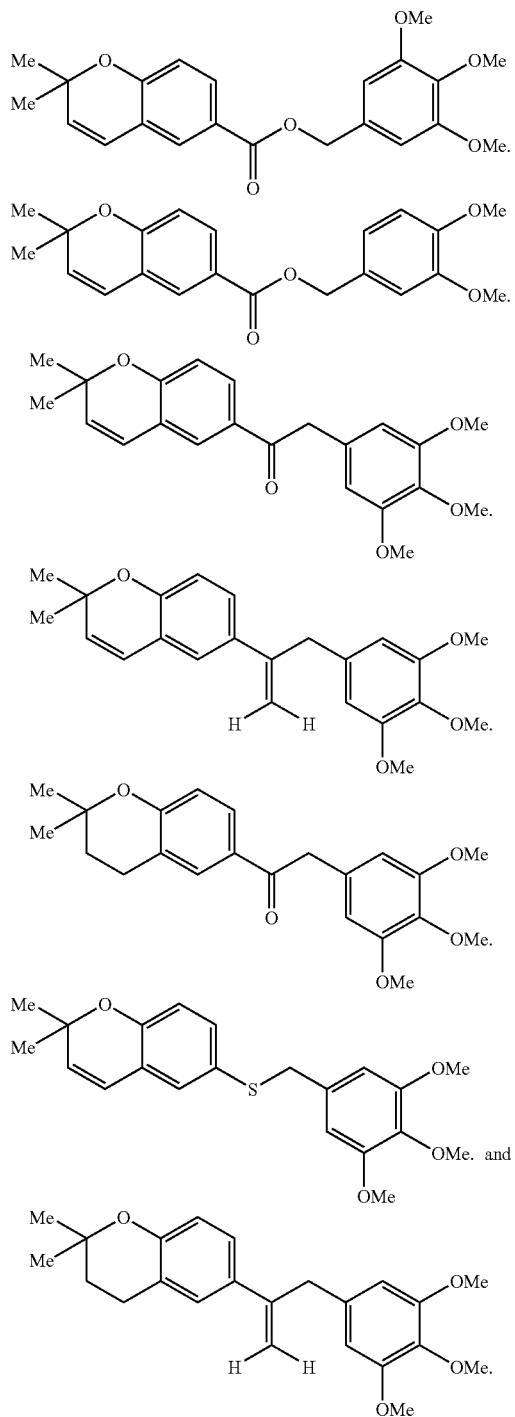

A fourth aspect of the invention is directed to a process for inhibiting an enzyme having NADH:ubiquinone oxidoreductase activity. The process employs the step of contacting such enzyme with a concentration of a compound sufficient to inhibit the said enzyme, wherein the compound is drawn from the first, second, or third aspect of the invention.

A fifth aspect of the invention is directed to a process for inhibiting the growth of a cancer cell. The process employs the step of contacting such cancer cell with a concentration of a compound sufficient to inhibit the growth of said cancer cell, wherein the compound is drawn from the first, second, or third aspect of the invention.

BRIEF DESCRIPTION OF DRAWINGS

FIG. 17 is a table of selected data for growth inhibition ($GI_{50}$) of compounds 55, 158, 165, and 178 in NCI cancer cell lines.

DETAILED DESCRIPTION

Figure 1:
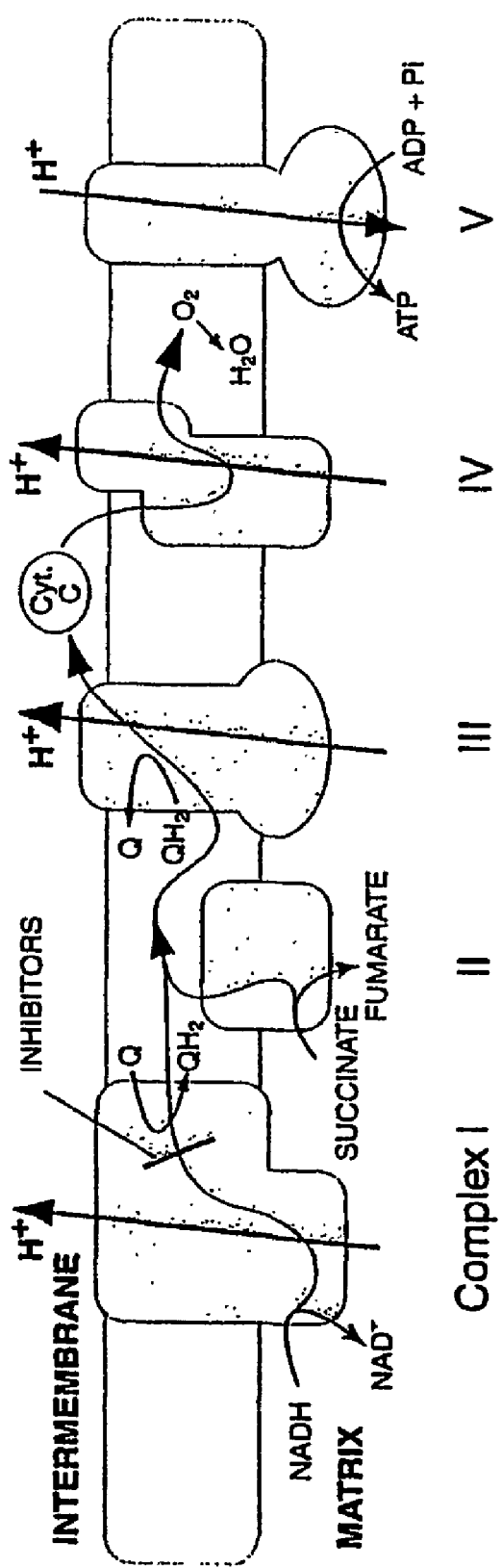
FIG. 1 is a cartoon drawing showing the role of NADH: ubiquinone oxidoreductase (Complex I) in oxidative phosphorylation.

Novel lead compounds were identified through the screening of natural product-like combinatorial libraries. Separation of the constituents of this resin provided the major components rotenone (1, FIG. 2) and deguelin (7, FIG. 3) along with minor constituents, including dehydrodeguelin (8), oxadehydrodeguelin (9), lonchocarpusone (10), 4-hydroxylonchocarpene (11), 4-hydroxy-3-methoxylonchocarpene (12), stilbenes 13-15, and isoflavones 16-18 (FIG. 3) among others. Inspection of natural products 7-18 revealed an interesting homology as all possessed a 2,2-dimethylbenzopyran motif linked to a terminal aromatic ring through a variety of molecular bridges. Despite the diversity in these bridging units, all of the compounds (7-18) inhibited Complex I activity in in vitro assays (Fang, N.; Casida, J. E. *J. Nat. Prod.* 1999, 62, 205-210; Fang, N.; et al. *Chem. Res. Toxicol.* 1997, 10, 853-858). Not surprisingly however, the potency of inhibition was strongly influenced by the orientation through which the "bridge" unit positioned the two ring systems with respect to each other. For example, deguelin ($IC_{50}$=6.9 nM) is almost 500-fold more active than lonchocarpusone ($IC_{50}$=3300 nM). Given this effect, it was envisioned that screening a benzopyran-based combinatorial library wherein this "bridge" unit was varied (i.e. structure 19, FIG. 3) might lead to the identification of interesting structure activity relationships (SAR), and potentially to new lead compounds in this series. Notably, it was anticipated that these lead compounds, synthesized through combinatorial chemistry, would be more amenable (as compared to the parent natural products) to further synthetic modifications as required for optimization of physical and pharmacological properties.

Figure 4:
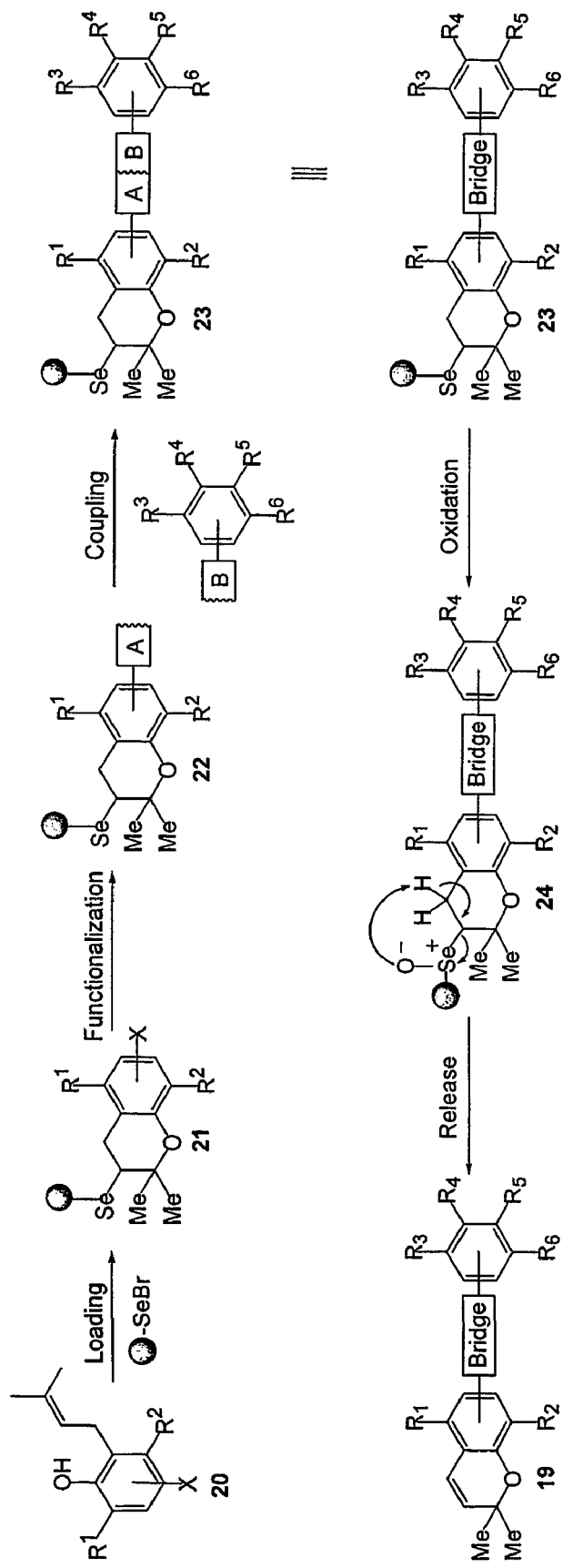
FIG. 4 is a scheme showing the general strategy for the solid phase combinatorial synthesis of natural product-like small molecules as potential inhibitors of NADH:ubiquinone oxidoreductase.
Figure 5A:
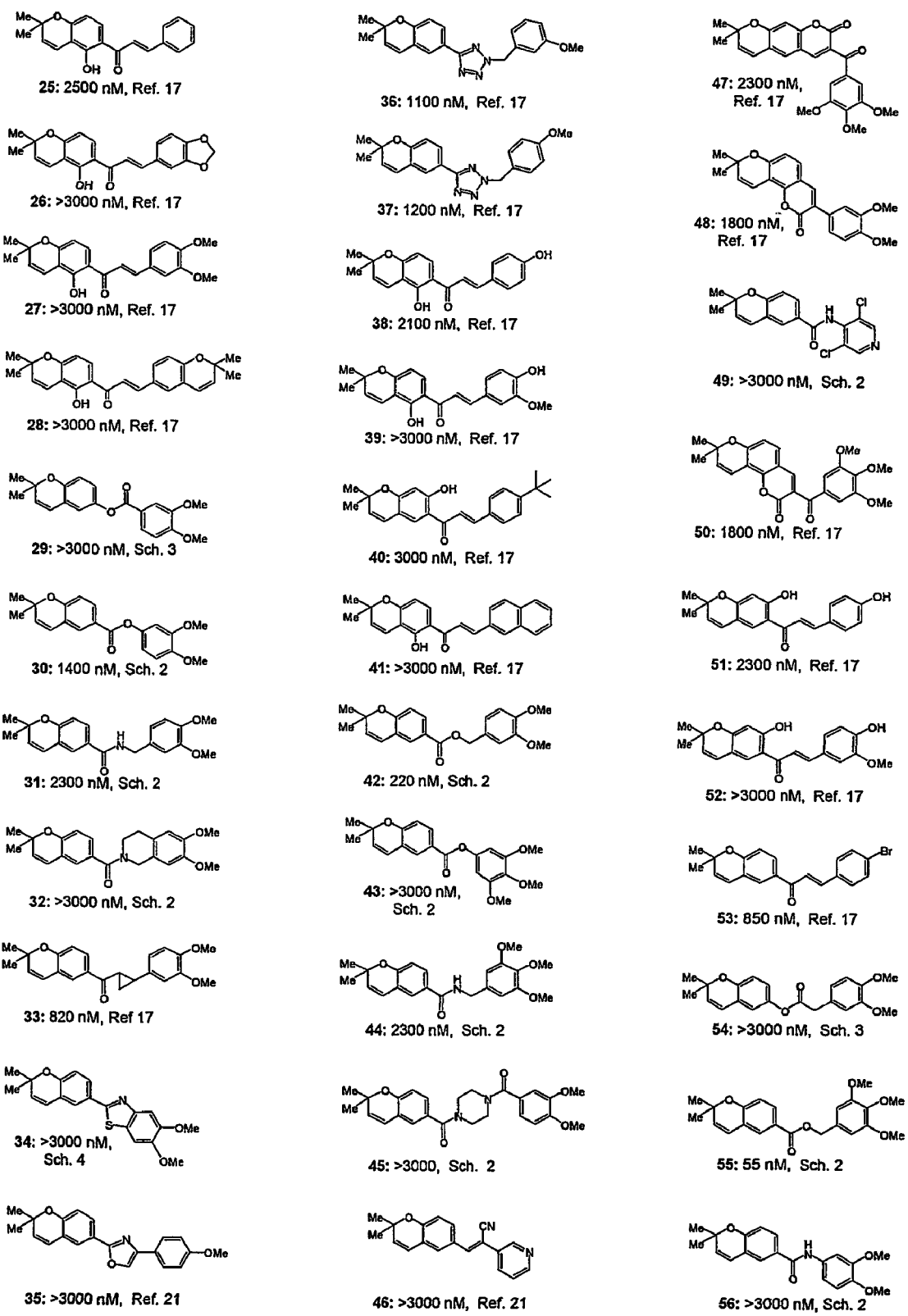
FIG. 5A shows the structures and $IC_{50}$ values of the screening library. The synthesis of individual members is described in the schemes and references indicated.
Figure 5B:
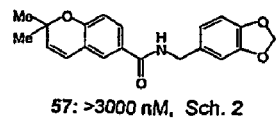
FIG. 5B shows more structures and $IC_{50}$ values of the screening library. The synthesis of individual members is described in the schemes and references indicated.
Figure 5B:
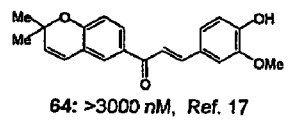
Figure 5B:
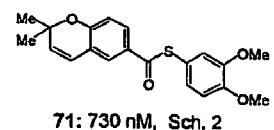
Figure 5B:
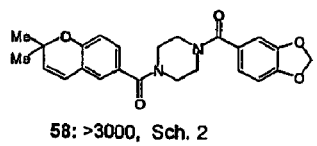
Figure 5B:
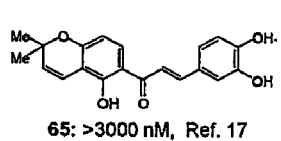
Figure 5B:
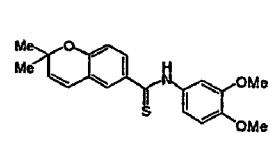
Figure 5B:
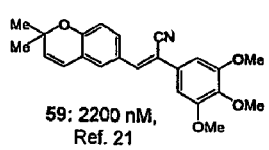
Figure 5B:
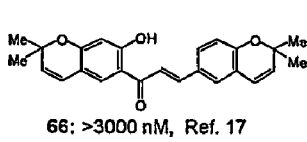
Figure 5B:
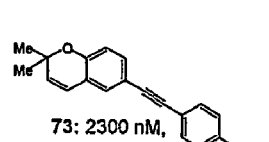
Figure 5B:
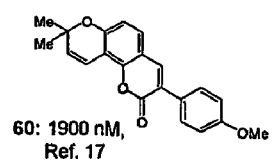
Figure 5B:
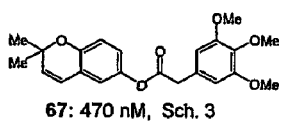
Figure 5B:
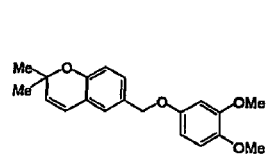
Figure 5B:
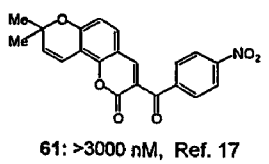
Figure 5B:
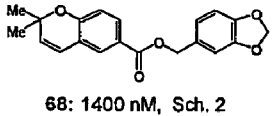
Figure 5B:
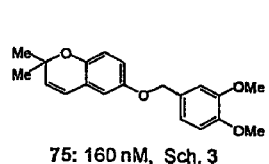
Figure 5B:
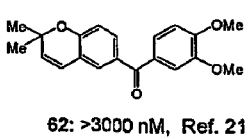
Figure 5B:
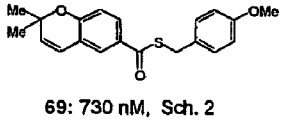
Figure 5B:
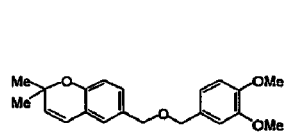
Figure 5B:
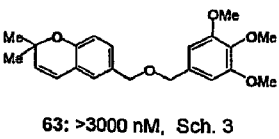
Figure 5B:
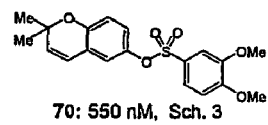

First Generation Discovery Library—The Bridge Region III (Compounds 25-76):

A 52-membered library was selected for preliminary screening as shown in FIGS. 5A and 5B. Members were selected so as to simultaneously evaluate both the nature of the "bridge" unit as well as the importance of substituents on the terminal aromatic ring system. Most members of this discovery library had been previously synthesized via a selenium-based, solid phase strategy as outlined FIG. 4. In this approach, a series of ortho-prenylated phenols (20) were cycloloaded (through a six-endo-trig electrophilic cyclization reaction) onto a polystyrene-based selenenyl bromide resin to afford resin-bound benzopyran scaffolds (21) (Nicolaou, K. C.; et al. *Angew. Chem. Int. Ed.* 2000, 39, 734-739; Nicolaou, K. C.; et al. *Angew. Chem. Int Ed.* 2000, 39, 739-743). These scaffolds were then functionalized and coupled with a second aromatic unit so as to create diverse bridge types (23). Upon completion, structures of type 23 could be further derivatized if necessary, and then released from the solid support by oxidation of the selenoether to the corresponding selenoxide which could undergo facile syn-elimination. The synthesis of compounds 25-28, 33, 35-41, 46-48, 50-54, 59-62, 64-66 and 73 (FIGS. 5A and 5B) via this solid phase route has been described previously (Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *Angew. Chem. Int. Ed.* 2000, 39, 734-739; Nicolaou, K. C.; et al. *Angew. Chem. Int. Ed.* 2000, 39, 739-743). Representative procedures for the solid phase synthesis of the remaining members of the described library are illustrated in Schemes 2-4. All library members for biological assay were chromatographically and spectroscopically ($^1$H-NMR) homogeneous.

Figure 6:
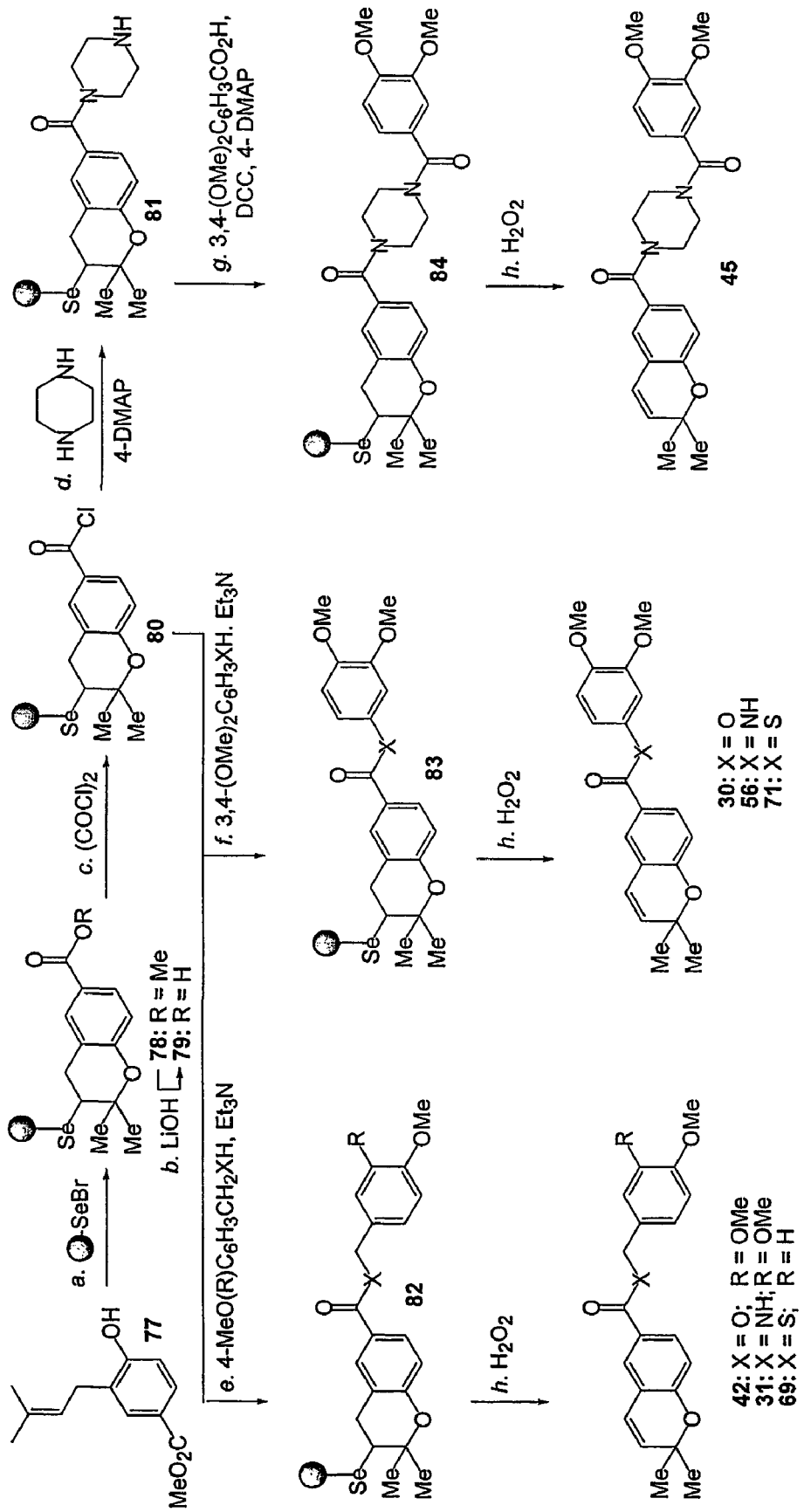
FIG. 6 gives representative procedures for the solid phase synthesis of amides, esters, and thioesters.

As shown in FIG. 6, the first type of library members to be constructed was a series of acyl derivatives. Initially, ortho-prenylated phenol 77 was cycloloaded onto a selenenyl bromide resin (Nicolaou, K. C.; et al. *Chem. Commun.* 1998, 1947-1948) to afford benzopyran scaffold 78. The methyl ester of 78 was then hydrolyzed (LiOH, THF:H$_2$O, 40° C.) to the corresponding carboxylic acid which was converted to acid chloride 80 by treatment with oxalyl chloride in the presence of catalytic amounts of DMF. This acid chloride then participated in three parallel reaction pathways. In the first sequence, treatment of acid chloride 80 with piperazine and 4-DMAP provided amide 81. The secondary amine of structure 81 was then coupled to 3,4-dimethoxybenzoic acid in the presence of DCC and 4-DMAP to provide diamide 84 which was released from the solid support by treatment with H$_2$O$_2$, giving diamide 45. In the second pathway, acid chloride 80 was treated (in parallel) with a series of aryl nucleophiles including 3,4-dimethoxyphenol, 3,4-dimethoxyaniline, and 3,4-dimethoxythiophenol to provide structures of type 83, which upon oxidative cleavage afforded ester 30, amide 56, and thioester 71, respectively. In the last pathway, acid chloride 80 was reacted with a series of benzylic nucleophiles including 3,4-dimethoxybenzyl alcohol, 3,4-dimethoxybenzyl amine, and 4-methoxy-α-toluene thiol to provide structures of type 82 which were oxidatively cleaved to afford ester 42, amide 31, and thioester 69, respectively. In addition to the representative compounds shown here, this procedure was repeated in an analogous and parallel manner to prepare compounds 32, 43-44, 49, 55, 57-58, and 68-69 (FIGS. 5A and 5B).

Figure 7:
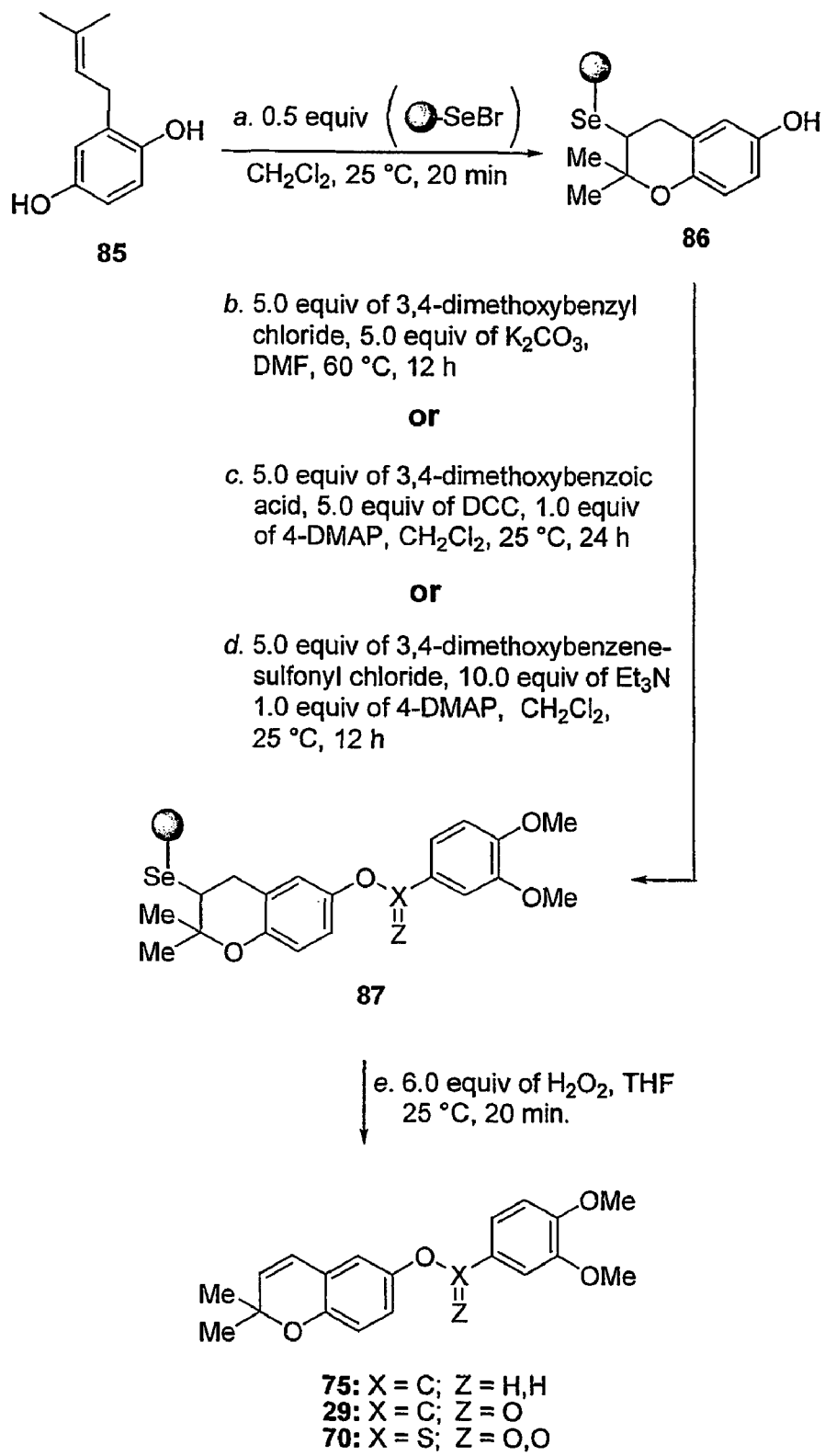
FIG. 7 shows representative procedures for the solid phase synthesis of ether (75), ester (29), and sulfonate (70) compounds.

As shown in FIG. 7, additional library members with other types of bridging units were constructed from a phenolic benzopyran system. Initially, resin-bound phenol 86 was prepared through the cycloloading of prenylated hydroquinone 85. Library members containing an ether-type bridge were then constructed by alkylation of 86 with 3,4-dimethoxyl benzyl chloride in the presence of K$_2$CO$_3$ followed by oxidative cleavage to afford ether 75. Ester derivatives were constructed by acylation of phenol 86 with 3,4-dimethoxybenzoic acid, DCC, and 4-DMAP to afford, after oxidative cleavage, ester 29. Lastly, sulfonate derivatives were constructed by treatment of phenol 86 with 3,4-dimethoxybenzenesulfonyl chloride, Et$_3$N, and 4-DMAP followed by oxidative cleavage to afford sulfonate 70. In addition to the representative compounds shown here, this procedure was also repeated in an analogous and parallel manner to prepare compounds 63, 67, 74, and 76 (FIGS. 5A and 5B).

Figure 8:
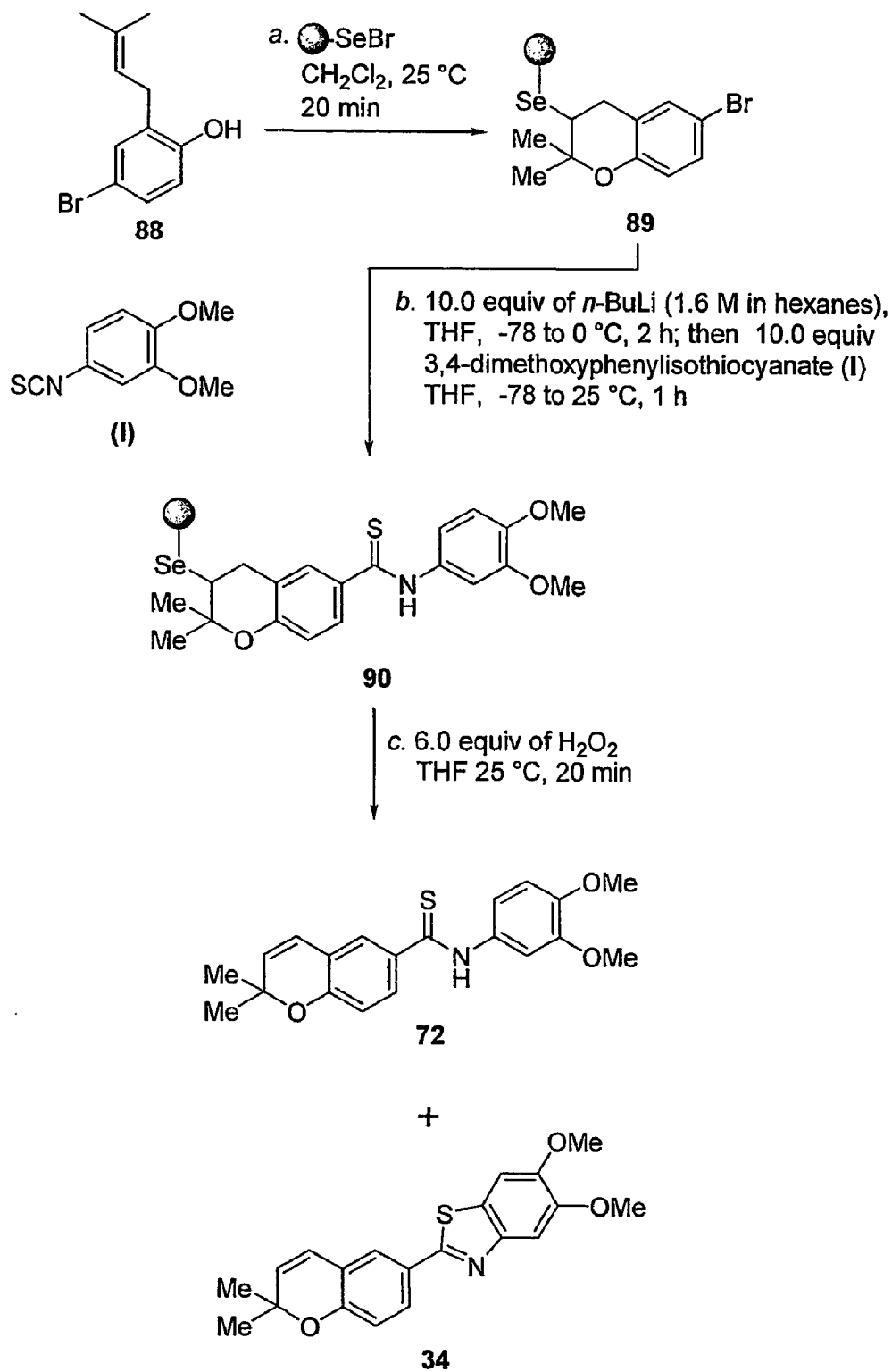
FIG. 8 gives the procedure for solid phase synthesis of thioamide (72) and thiazole (34) systems.

As shown in FIG. 8, several sulfur-containing library members were synthesized through a halogen-metal exchange reaction. Initially, bromophenol 88 was cycloloaded onto the selenenyl bromide resin to give benzopyran 89. Aryl bromide 89 was subjected to a halogen metal exchange reaction by treatment with n-BuLi at −78° C. and then warming to 0° C. over 2 h at which time 3,4-dimethoxyphenylisothiocyanate was added. Cleavage of the supposed thioamide 90 by treatment with H$_2$O$_2$ unexpectedly afforded a separable mixture of thioamide 72 and thiazole 34 the latter being presumably formed as a result of excess base present in the halogen-metal exchange reaction.

This primary library was screened for inhibitory potency against NADH:ubiquinone oxidoreductase activity as described below. This screening revealed several structure-activity trends (summarized in FIG. 9 and discussed in detail in Section 6) which ultimately provided esters 42 and 55 as lead compounds. As described below, a series of focused libraries were then synthesized using a combination of solid and solution phase chemistry in an attempt to evaluate particular structural sub-regions (denoted I-IV in FIG. 9) of the lead structure, thus allowing structure activity relationships to be developed.

First Focused Library—Aryl Substituents—Regions II and IV (Compounds 91-127):

The first of these follow-up libraries focused on regions II and IV of the lead structure. Of particularly interest was how substituent patterns on these two aromatic systems would effect inhibitory activity. Hence a series of esters (91-127, FIG. 15) were synthesized in parallel on solid support using an identical protocol to that described in FIG. 6. The aromatic building blocks employed contained a variety of substituents including alkyl groups, halogens, alkoxy groups, hydroxyl groups, alcohols, and nitro groups in order to assess both steric and electronic effects.

Figure 10:
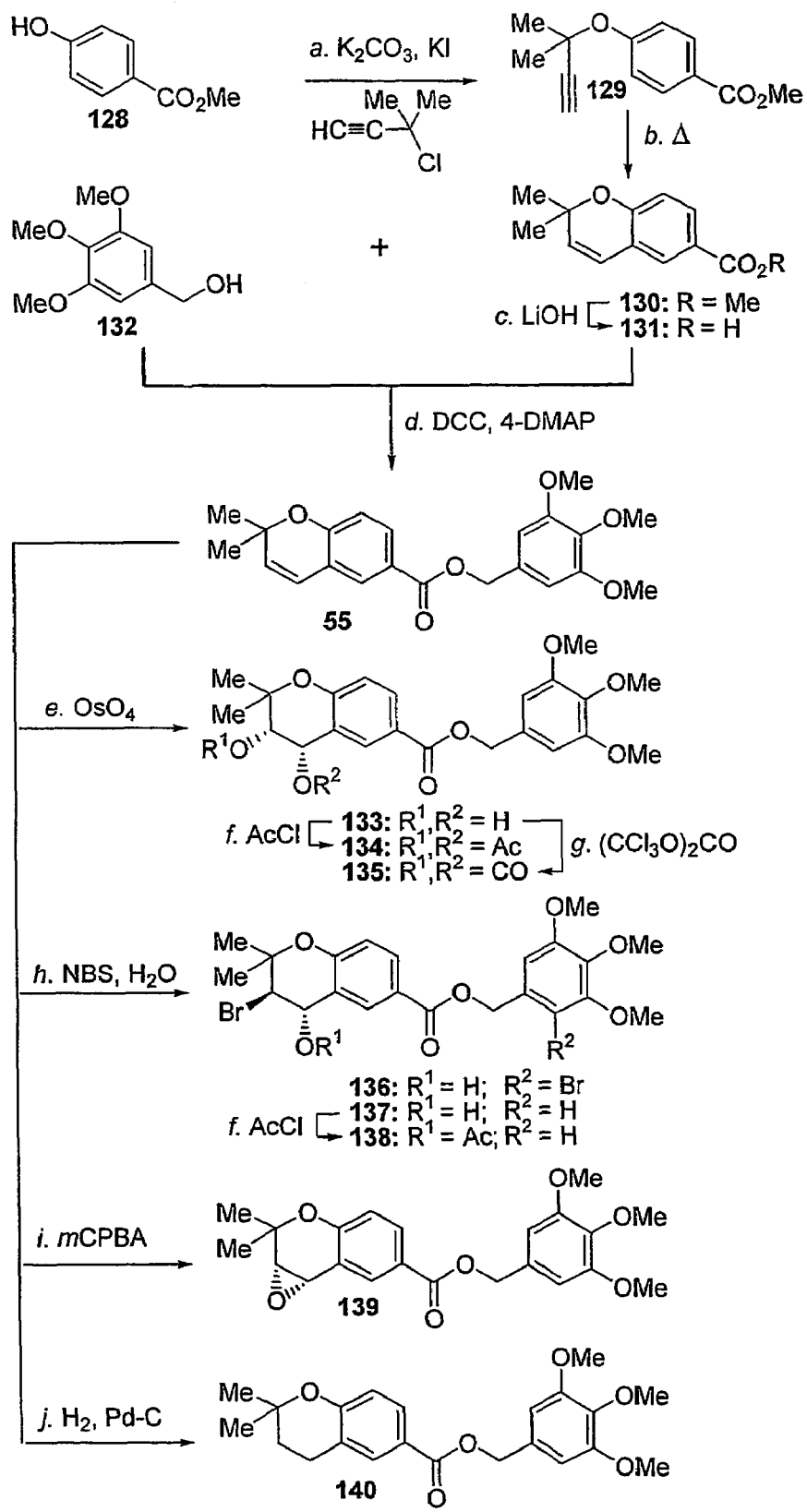
FIG. 10 is a scheme showing the solution phase synthesis of 3,4,5-trimethoxybenzyl ester (55) and modified pyran analogs and their biological activities.

Second Focused Library—Dimethylpyran Modifications—Region I (Compounds 133-140):

The synthesis of the second of the follow-up libraries relied upon solution phase chemistry and was designed so as to evaluate how modifications in the pyran ring system might effect biological activity. Thus, as shown in FIG. 10, lead ester 55 was first resynthesized on large scale from 4-hydroxymethyl benzoate 128 by initial O-alkylation with 3-chloro-3-methyl-1-butyne to give ether 129 (Bell, D.; et al. *Synthesis* 1995, 707-712). Heating of alkyne 129 in N,N-diethylaniline at 195° C. for 1 h induced an aromatic Claisen rearrangement to provide benzopyran 130 in quantitative yield (Bell, D.; et al. *Synthesis* 1995, 707-712). The methyl ester of 130 was hydrolyzed (LiOH, THF:H$_2$O, 40° C., 12 h) to the free acid 131 which was coupled to 3,4,5-trimethoxybenzyl alcohol in the presence of DCC and 4-DMAP to furnish ester 55. With the ester 55 in hand, several derivatization reactions were employed to provide the series of pyran-modified analogs 133-140. First, the olefin of ester 55 was dihydroxylated (Fenwick, A. E. *Tetrahedron Left.* 1993, 34, 1815-1818) (cat OsO$_4$, NMO, t-BuOH:THF:H$_2$O, 25° C., 6 h) to afford diol 133 which was subsequently acetylated to diacetate 134 and reacted with triphosgene to provide carbonate 135. In a second event, ester 55 was treated (Gabbutt, C. D.; et al. *J. Chem. Soc. Perkin Trans. I.* 1994, 1733-1737) with NBS in the presence of H$_2$O to provide a mixture of bromohydrins 136 and 137 as a result of partial bromination of the terminal aromatic ring (i.e. structure-136). Bromohydrin 137 was subsequently acetylated (AcCl, pyridine, CH$_2$Cl$_2$, 25° C., 1 h) to afford acetate 138. Additionally, ester 55 was converted to the corresponding epoxide 139 by treatment with m-CPBA (Buckle, D. R.; et al. *J. Med. Chem.* 1990, 33, 3028-3034). Finally, the olefin of ester 55 was saturated by hydrogenation over 10% Pd-C to provide the corresponding saturated pyran system 140.

Figure 11:
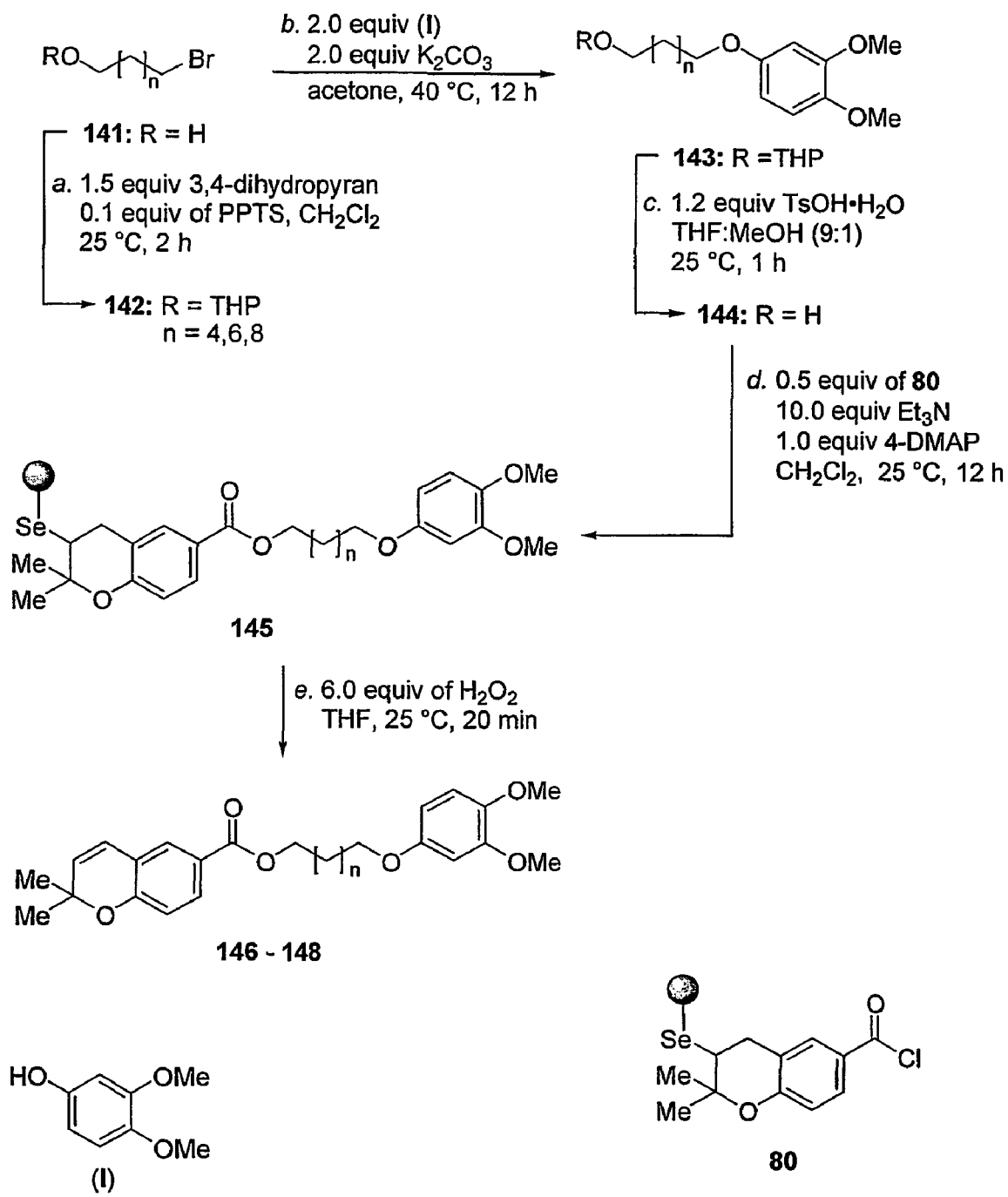
FIG. 11 is a scheme showing the synthesis of long chain 3,4-dimethoxyphenyl esters.
Figure 12:
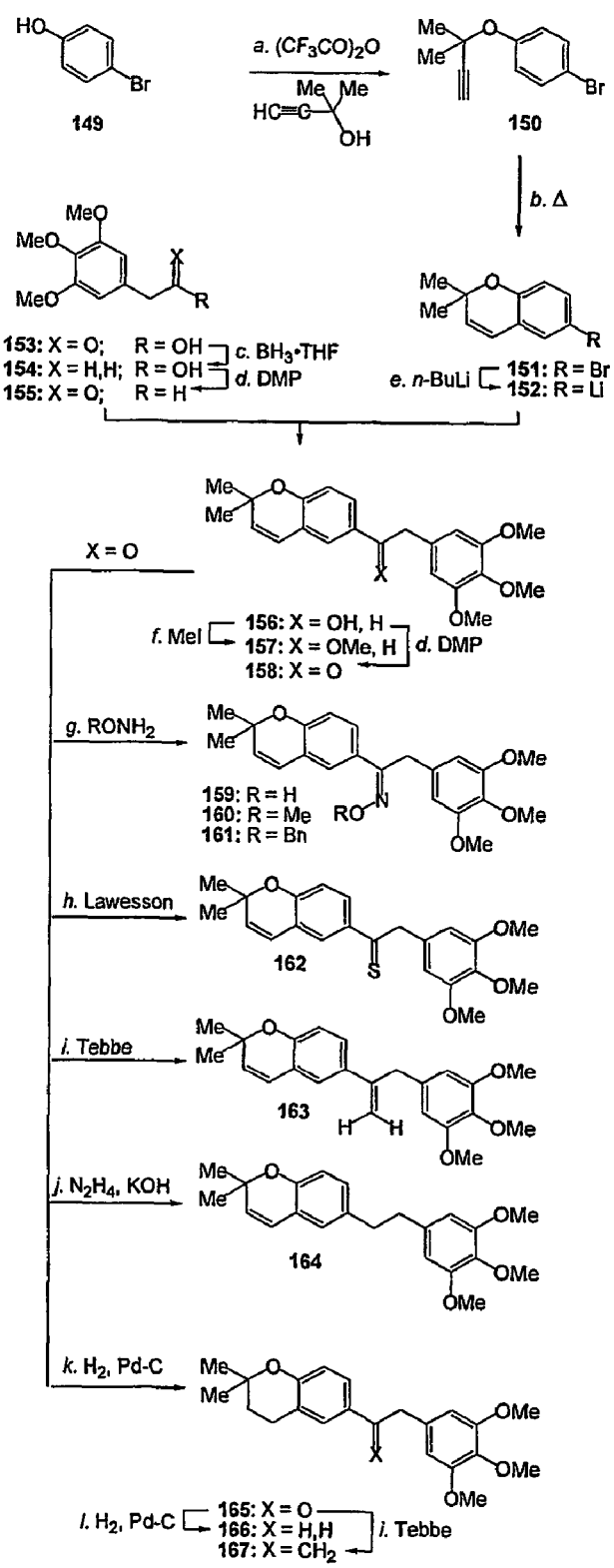
FIG. 12 is a scheme showing the solution phase synthesis of 3,4,5-trimethoxyphenyl ketone (158) and analogs thereof.
Figure 15A:
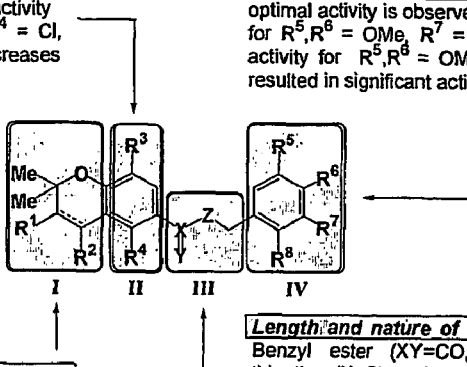
FIG. 15 is a graphical summary of structure activity trends observed for benzopyran-based inhibitors of NADH: ubiquinone oxidoreductase.

Third Focused Library—The Bridge Region III (Compounds 146-179):

A final library in this series sought to further investigate the nature of the bridge unit. Of particular interest was the effects of length, structure, and polarity of this bridge as illustrated in Schemes 6-9. In order to access the relationship between bridge length and biological activity, a set of longer chain analogs 146-148 was synthesized as illustrated in FIG. 11 where alcohols of type 141 were prepared by alkylation of the corresponding bromoalcohols and then coupled to resin-bound acid chloride 80 as previously described. Subsequently, it was sought to determine whether or not the ester functionality itself was optimal as a bridge unit. This was accomplished by the solution phase synthesis of various other linking units, including ketones, oximes, thioketones, alkyl chains, thioethers, and sulfones as shown in Schemes 7-9 and Table 3. As illustrated in FIG. 12, various keto analogs and their derivatives were constructed starting from 4-bromophenol 149. Following the procedure of Ding, 4-bromophenol (149) was alkylated with the in-situ generated trifluoroacetate of 2-methyl-3-butyn-2-ol to afford 150, which was heated to 195° C. in N,N-diethylaniline inducing an aromatic Claisen rearrangement and providing benzopyran 151 in quantitative yield (Ding, C. Z. *Syn. Commun.* 1996, 26, 4267-4273). Subsequent treatment of 151 with n-BuLi afforded aryl lithium 152, which was immediately quenched by addition of aldehyde 155 (synthesized from phenylacetic acid 153, as indicated in FIG. 12) to provide benzyl alcohol 156. Dess-Martin periodinane oxidation of alcohol 156 afforded ketone 158. Incidentally, the methyl ether analog of alcohol 156, compound 157, was also synthesized from alcohol 156 via alkylation with MeI in the presence of NaH. With ketone 158 available, a series of modified keto-analogs were then constructed. Thus, oximes 159-161 were prepared by condensation of ketone 158 with the appropriate hydroxy or alkoxy amines in the presence of $K_2CO_3$. Thioketone 162 was prepared by reaction of ketone 158 with Lawesson's reagent in toluene at 100° C. for 3 h, whereas the corresponding olefin analog 163 was constructed by treatment of ketone 158 with Tebbe reagent. Wolf-Kishner reduction of 158 ($N_2H_4$, KOH, Δ) afforded the alkyl variant 164, while hydrogenation over 10% Pd-C provided the saturated version (i.e. 165) of ketone 158 as well as of analogs 163 and 164 (i.e. 167 and 166, respectively). Additional variations of ketone 158 were also constructed to address the importance of tether length and bridge substitution. These analogs were synthesized via an analogous protocol to that shown in FIG. 12 and their structures (170-174) are illustrated in FIG. 15.

Figure 13:
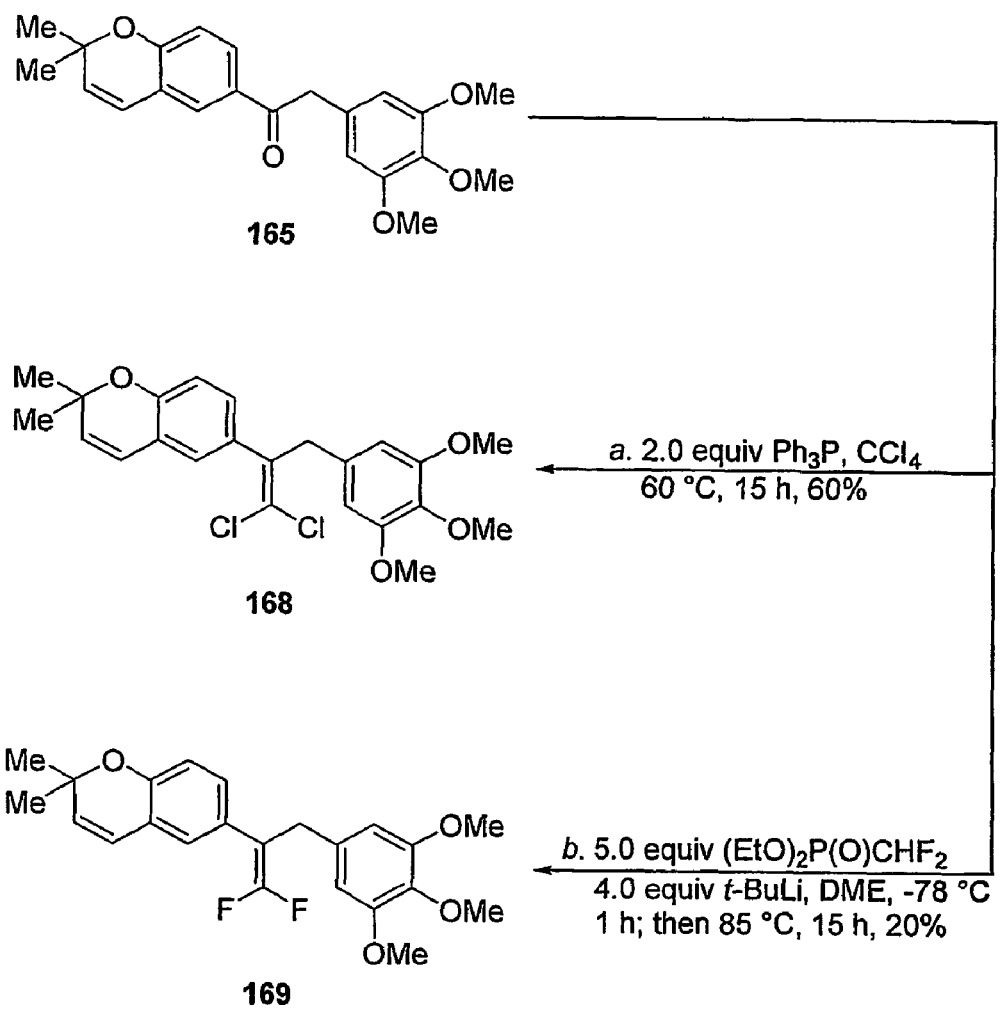
FIG. 13 shows the solution phase synthesis of difluoro- and dichlorostyrene analogues 168 and 169.

Several halogenated derivatives of styrene 163 were also prepared as illustrated in FIG. 13. Hence, ketone 165 was treated with $Ph_3P$ in $CCl_4$ at 60° C. to afford dichloro-analog 168 (Clement, B. A.; Soulen, R. L. *J. Org. Chem.* 1974, 39, 97-98). Additionally, ketone 165 was added to a solution of diethyl(difluoromethyl)phosphonate and t-BuLi in DME at −78° C. and then warmed to 25° C., and finally to 85° C. to ultimately afford difluoro-analog 169 (Piefre, S. R.; Cabanas, L. *Tetrahedron Lett.* 1996, 37, 5881-5884).

Figure 14:
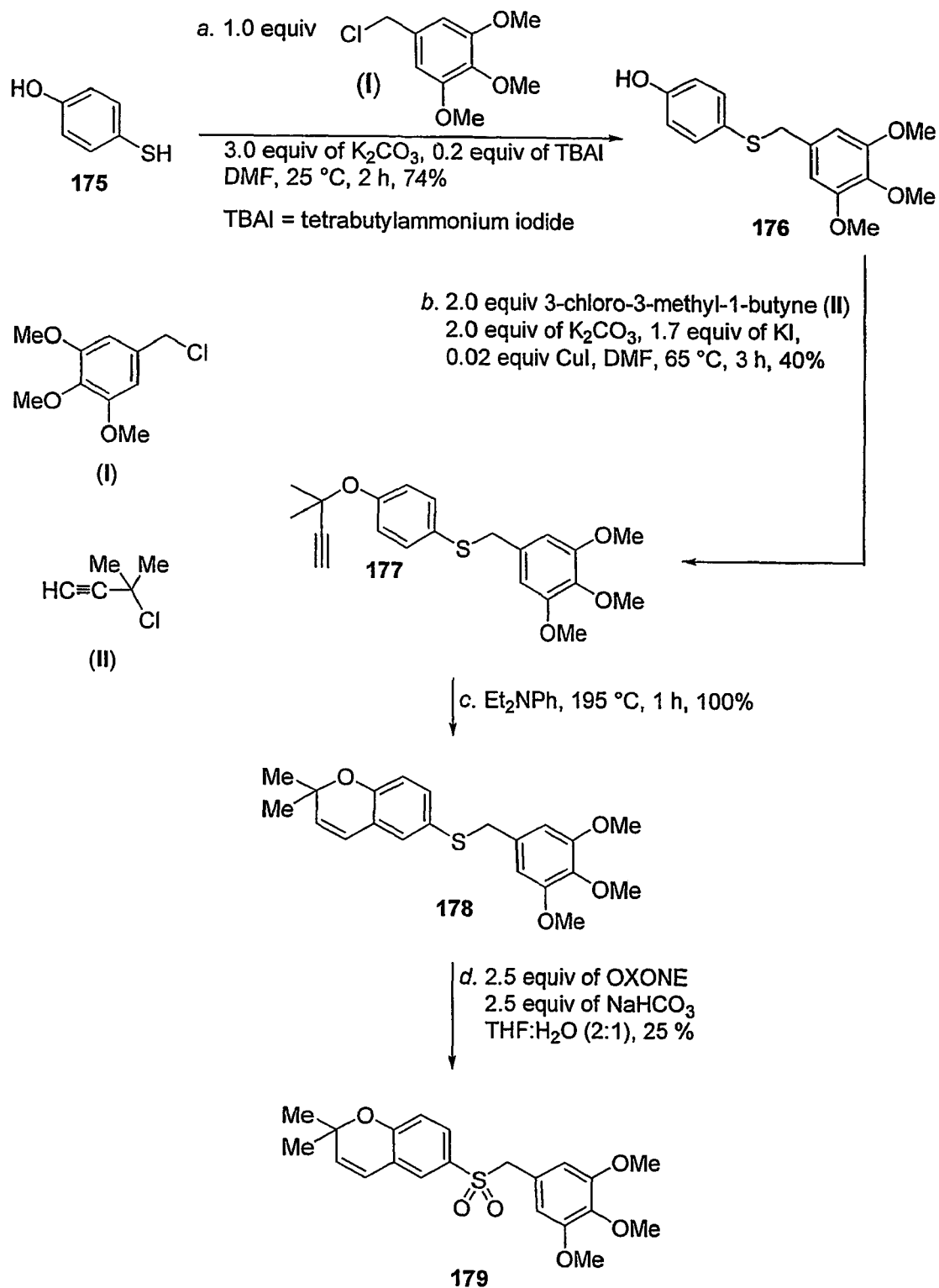
FIG. 14 shows the solution phase synthesis of 3,4,5-trimethoxyphenylthioether 178 and 3,4,5-trimethoxyphenylsulfone 179.

A final set of compounds for addressing the nature of the bridge unit was prepared as illustrated in FIG. 14 in an attempt to optimize the activity observed for ether 75 during screening of the first generation library. The thioether variant of this analog was prepared from 4-mercaptophenol (175) by selective S-alkylation with 3,4,5-trimethoxybenzyl chloride and $K_2CO_3$ to provide thioether 176 (Sato, M.; et al. *Eur. J. Med. Chem.* 1995, 30, 403-414). Subsequent O-alkylation was effected with 3-chloro-3-methyl-1-butyne to give alkynyl ether 177. Heating of alkyne 177 in N,N-diethylaniline at 195° C. for 1 h induced an aromatic Claisen rearrangement furnishing benzopyran 178 in quantitative yield. A portion of thioether 178 was then oxidized with OXONE® to afford the corresponding sulfone 179.

Structure Activity Relationships (SAR):

SAR optimization was carried out on each of the four regions (I-IV) of interest guided by the inhibitory potency for NADH:ubiquinone oxidoreductase activity in vitro using bovine heart electron transport particles (see Singer (Singer, T. P. (1974). In *Methods of Biochemical Analysis* (Glick, D. ed., Wiley New York), 22, pp. 123-175) for details).

Figure 9:
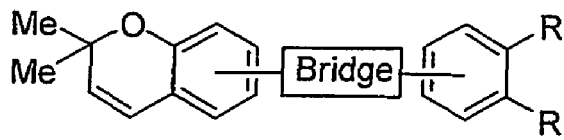
FIG. 9 is a table giving a summary of biological data from evaluation of the first generation library and proposed lead structures.
Figure 9:
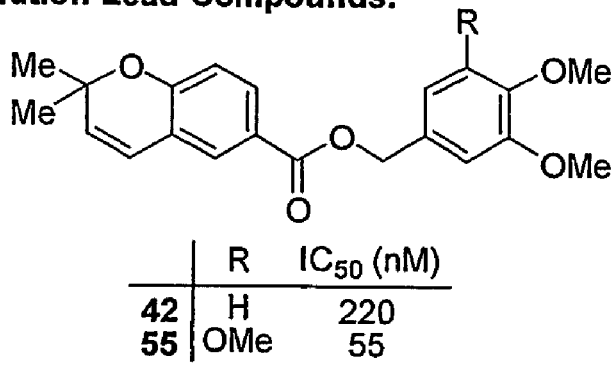
Figure 9:
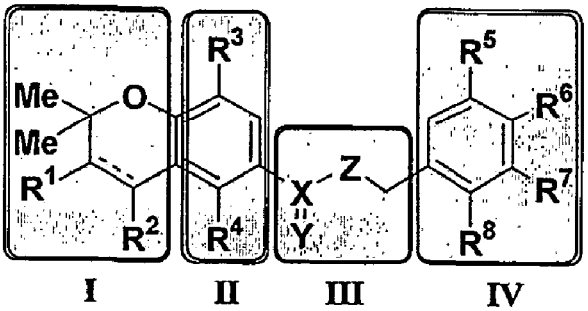

The original library emphasizing bridge region III gave the $IC_{50}$ values for 25-76 indicated in FIGS. 5A and 5B and the SAR summarized in FIG. 9. Compounds containing a conjugated and/or rigid bridging unit (i.e. chalcones, stilbenes, coumarins, heterocycles, or alkynes) exhibited low activity ($IC_{50}$>1000 nM) similar to those for most of the benzopyran-containing natural products (11-15, FIG. 3). More interestingly, methylenes in the bridge unit, for greater conformational flexibility, resulted in higher activity dependent on the substituent pattern on the terminal aromatic ring, i.e. 220 nM $IC_{50}$ for 3,4-dimethoxybenzyl esters 42 and 55 nM $IC_{50}$ for 3,4,5-trimethoxybenzyl ester 55, the most potent inhibitor in the screening library. The corresponding amides (31 and 44, FIGS. 5A and 5B), presumably more polar than their ester counterparts, were significantly less active (40-fold and 10-fold respectively), suggesting the possible importance of lipophilicity at region III.

The first of the focused libraries (91-127, FIG. 15) examined the substituent patterns for aromatic regions II and IV. Somewhat suprisingly, only esters 110 ($IC_{50}$=44 nM) and 120 ($IC_{50}$=49 nM) exhibited marginally improved activity over the original 3,4,5-trimethoxybenzyl ester 55 ($IC_{50}$=55 nM). Varying substituents on the aromatic benzopyran ring only moderately influenced activity, e.g. introducing a halogen at $R^1$ (42→104; 55→112) or a hydroxyl group at $R^2$ (55→110). A bulky substituent of the oxygen at $R^4$ (42→121; 55→122) resulted in only slightly diminished inhibitory activity implying the greater importance of electronic rather than steric factors at this position. More generally, the 3,4,5-trimethoxyphenyl substituent is at or near the optimum for region IV.

The second focused library considered modifications of the pyran ring system (FIG. 15). Introduction of a polar functionality on the pyran ring (i.e. 133 and 134) significantly compromised activity, and less polar substituents (i.e. 135-139) afforded no improvements. However, conversion to its saturated counterpart (55→140) resulted in a compound which retained potent biological activity ($IC_{50}$=53 nM) yet was presumably metabolically more stable owing to the removal of the oxidatively-sensitive pyran olefin.

A final focused library reexamined the bridging unit (region III) with keto-analogs revealing several interesting trends (FIG. 15). First, ketone 158 was more active than the original ester lead with an $IC_{50}$ value of 39 nM. Alcohol 156, ether 157, oximes 159-161, thioketone 162, and compound 164 were significantly less active than ketone 158. Removal of the pyran olefin of ketone 158 via hydrogenation provided compound 165 which was almost twice as active as the parent olefin with an $IC_{50}$ value of 24 nM. Intriguingly, conversion of the ketone to the corresponding olefin also increased activity as demonstrated for compound 163 ($IC_{50}$=19 nM) and its saturated pyran counterpart 167 ($IC_{50}$=18 nM). Substitution of the olefin protons with halogens (i.e. structures 168 and 169) resulted in dichloro and difluoro analogs with reduced activity ($IC_{50}$ values 2700 and 48 nM, respectively). On a separate note, thioether 178 was quite active with an $IC_{50}$ of 43 nM, whereas the more polar sulfone 179 was inactive.

The overall results summarized in FIG. 15 prompted selection of 55, 158, 163, 165, 167 and 178 (FIG. 16) for further biological testing. Despite their structural simplicity, the inhibitory activity of these compounds approached that for the most potent natural product in this series, namely deguelin (7, FIG. 3) with an $IC_{50}$ value of 6.9 nM. Moreover, unlike the structurally-complex deguelin, these lead compounds were simple to construct and thus could be readily modified to improve pharmacological properties, solubility or biostability.

The identified lead compounds were evaluated in several cell-based assays. The first involved determination of the cytotoxic concentrations ($LC_{50}$ values) in MCF-7 human epithelial breast cancer cells using the MTT assay (Fang, N.; et al. *Chem. Res. Toxicol.* 1997, 10, 853-858). The six compounds tested showed low cytotoxicity in the MCF-7 cells ($LC_{50}$>30000 nM). Secondly, compounds 55, 158, 165 and 178 were also evaluated in the NCI 60-cell cancer panel for the concentration leading to 50% growth inhibition ($GI_{50}$; see representative examples in FIG. 17) (Monks, A.; et al. *J. Natl. Cancer Inst.* 1991, 83, 757-766). Moderate to good activity was observed in growth inhibition in various cell lines. The leukemia cells are generally the most sensitive ($GI_{50}$ from 750 to 2850 nM) and the CNS cells the least sensitive ($GI_{50}$ from 4380 to 12900 nM) to these compounds and the overall potency order is 165>178>158>55. The combination of rather potent growth inhibition and possibly low cytotoxicity makes these compounds interesting lead structures as potential chemopreventive/chemotherapeutic agents.

Rationalization of SAR by Molecular Modeling:

In an effort to better understand the molecular basis for the potent inhibitory activity exhibited by several of these compounds, molecular modeling studies were undertaken. Specifically, the 3-dimensional orientation of these leads were compared to that of the structurally more complex natural product deguelin (Eadey, F. G.; et al. *FEBS Lett.* 1987, 219, 108-112) (7, FIG. 3) which remains the most potent compound in the benzopyran series. The semi-rigid structure of deguelin (7) was first minimized with molecular mechanics calculations (Insight II, CFF93 force field (Hwang, M. J.; et al. *J. Am. Chem. Soc.* 1994, 116, 2515-2525)) which provided its lowest energy conformation as the skewed structure. Subsequently, ester 55 (FIG. 16) and ketone 158 (FIG. 16) were also minimized. Comparison of these minimized structures revealed that the second lowest energy conformation of ester 55 and the lowest energy conformation of ketone 158 resembled quite closely the bent configuration of deguelin 7. In fact, the overlay of the lowest energy conformations of deguelin 7 and ketone 158, illustrate a strong homology between the two structures. The fact that the lowest energy configuration of ketone 158 best matched deguelin, whereas the less populated second lowest energy configuration of ester 55 matched deguelin was consistent with the fact that ketone 158 with an $IC_{50}$ value of 39 nM was more potent than ester 55 which possessed an $IC_{50}$ value of 55 nM.

DETAILED DESCRIPTION OF FIGURES

FIG. 1 is a cartoon drawing showing the role of NADH:ubiquinone oxidoreductase (Complex I) in oxidative phosphorylation. NADH:ubiquinone oxidoreductase is the first of three large enzyme complexes located in the cell's inner mitochondrial membrane which form the electron transport chain that carries electrons from NADH to molecular oxygen during oxidative phosphorylation. Complex I is the most intricate enzyme known, consisting of over 40 individual protein subunits with one non-covalently bound flavin mononucleotide and at least five iron-sulfur clusters. This enzyme serves and essential role in cellular physiology such that structural or functional deficiencies in it have been implicated in the pathogenesis of diseases such as Parkinson's, focal dystonia, and Leber's hereditary optic neuropathy.

Figure 2:
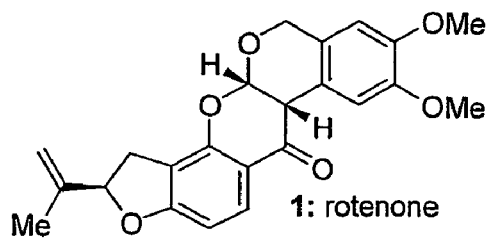
FIG. 2 shows structures of representative natural and synthetic inhibitors of NADH:ubiquinone oxidoreductase.
Figure 2:
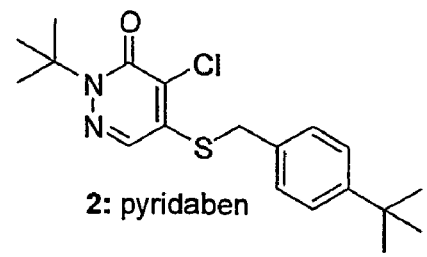
Figure 2:
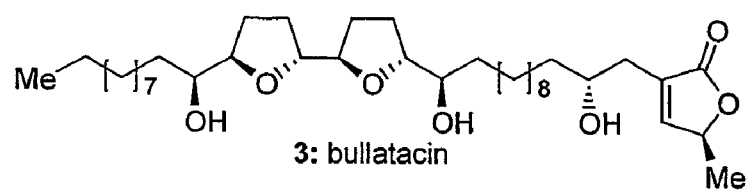
Figure 2:
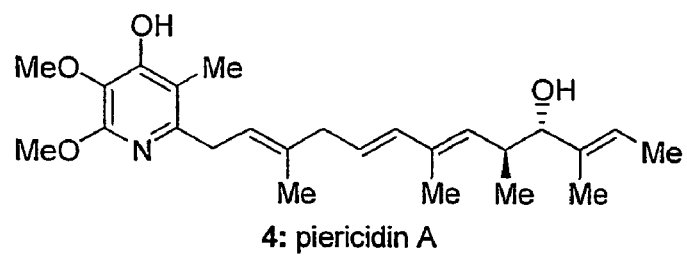
Figure 2:
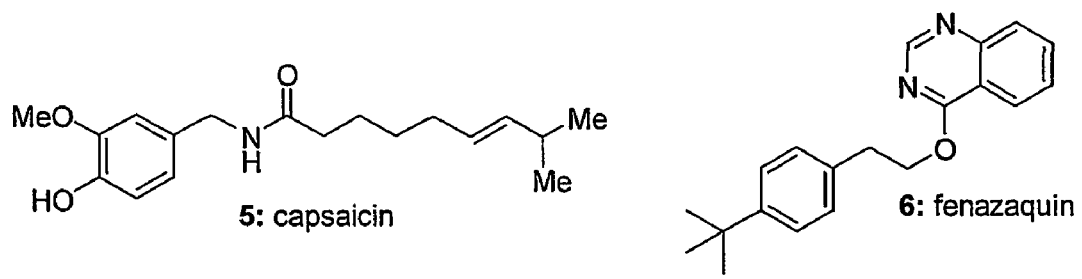
Figure 2:
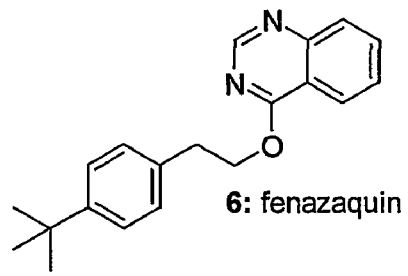

FIG. 2 shows structures of representative natural and synthetic inhibitors of NADH:ubiquinone oxidoreductase. These compounds have found a variety of uses. They have been used to elucidate the role of this enzyme in normal cell physiology. Develop structure activity relationships (SAR) of inhibitors of this enzyme to gain important insights into the functional architecture of this enzyme system. Rotenone is a major component of Cubé resin, an extract of the roots of Lonchocarpus utilis and urucu, which has been used as a botanical insecticide for decades.

Figure 3:
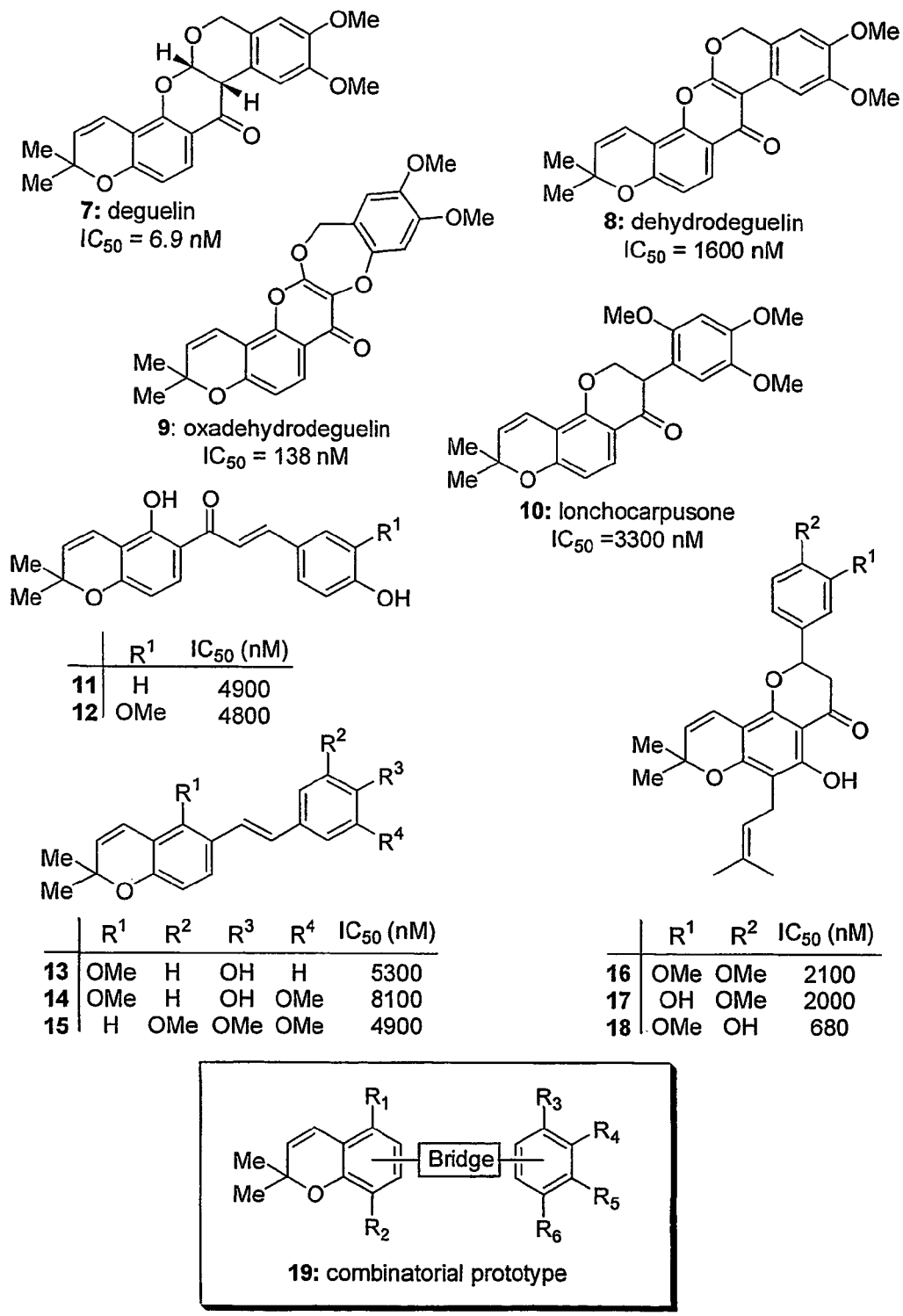
FIG. 3 shows selected natural product inhibitors (7-18) of NADH:ubiquinone oxidoreductase isolated from Cubé resin and combinatorial library prototype (19).

FIG. 3 shows selected natural product inhibitors (7-18) of NADH:ubiquinone oxidoreductase isolated from Cubé resin and combinatorial library prototype (19). Deguelin (7) is a major component of this resin along with minor constituents like dehydrodeguelin (8), oxadehydrodeguelin (9), lonchocarpusone (10), 4-hydroxyloncho-carpene (11), 4-hydroxy-3-methoxylonchocarpene (12), stilbenes (13-15), and isoflavones (16-18). Examination of natural products 7-18 revealed an interesting homology as all possessed a 2,2-dimethylbenzopyran motif linked to a terminal aromatic ring through a variety of functional bridges.

FIG. 4 is a scheme showing the general strategy for the solid phase combinatorial synthesis of natural product-like small molecules as potential inhibitors of NADH:ubiquinone oxidoreductase. The first generation, 52-membered library was selected for preliminary screening. Members were selected so as to simultaneously evaluate both the nature of the "bridge" unit as well as the importance of substituents on the terminal aromatic ring system. Most members of this discovery library had been previously synthesized via a selenium-based, solid phase strategy as outlined Scheme 1. In this approach, a series of ortho-prenylated phenols (20) were cycloloaded (through a six-endotrig electrophilic cyclization reaction) onto a polystyrene-based selenenyl bromide resin to afford resin-bound benzopyran scaffolds (21) (Nicolaou, K. C.; et al. *Angew. Chem. Int Ed.* 2000, 39, 734-739; Nicolaou, K. C.; et al. *Angew. Chem. Int. Ed.* 2000, 39, 739-743). These scaffolds were then functionalized and coupled with a second aromatic unit so as to create diverse bridge types (23). Upon completion, structures of type 23 could be further derivatized if necessary, and then released from the solid support by oxidation of the selenoether to the corresponding selenoxide which could undergo facile syn-elimination. The synthesis of compounds 25-28, 33, 35-41, 46-48, 50-54, 59-62, 64-66 and 73 via this solid phase route has been described previously (Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *Angew. Chem. Int. Ed.* 2000, 39, 734-739; Nicolaou, K. C.; et al. *Angew. Chem. Int. Ed.* 2000, 39, 739-743).

FIG. 5A shows the structures and $IC_{50}$ values of the screening library. The synthesis of individual members is described in the schemes and references indicated. The synthesis of compounds 25-28, 33, 35-41, 46-48, 50-54, 59-62, 64-66 and 73 via this solid phase route has been described previously (Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *Angew. Chem. Int. Ed.* 2000, 39, 734-739; Nicolaou, K. C.; et al. *Angew. Chem. Int. Ed.* 2000, 39, 739743).

FIG. 5B shows more structures and $IC_{50}$ values of the screening library. The synthesis of individual members is described in the schemes and references indicated. The synthesis of compounds 25-28, 33, 35-41, 46-48, 50-54, 59-62, 64-66 and 73 via this solid phase route has been described previously (Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *J. Am. Chem. Soc.* 2000, 122, in press; Nicolaou, K. C.; et al. *Angew. Chem. Int. Ed.* 2000, 39, 734-739; Nicolaou, K. C.; et al. *Angew. Chem. Int. Ed.* 2000, 39, 739-743).

FIG. 6 gives representative procedures for the solid phase synthesis of amides, esters, and thioesters. This series of acyl derivatives was the first type of library members to be constructed. Initially, ortho-prenylated phenol 77 was cycloloaded onto a selenenyl bromide resin (Nicolaou, K. C.; et al. *Chem. Commun.* 1998, 1947-1948) to afford benzopyran scaffold 78. The methyl ester of 78 was then hydrolyzed (LiOH, THF:$H_2O$, 40° C.) to the corresponding carboxylic acid which was converted to acid chloride 80 by treatment with oxalyl chloride in the presence of catalytic amounts of DMF. This acid chloride then participated in three parallel reaction pathways. In the first sequence, treatment of acid chloride 80 with piperazine and 4-DMAP provided amide 81. The secondary amine of structure 81 was then coupled to 3,4-dimethoxybenzoic acid in the presence of DCC and 4-DMAP to provide diamide 84 which was released from the solid support by treatment with $H_2O_2$, giving diamide 45. In the second pathway, acid chloride 80 was treated (in parallel) with a series of aryl nucleophiles including 3,4-dimethoxyphenol, 3,4-dimethoxyaniline, and 3,4-dimethoxythiophenol to provide structures of type 83, which upon oxidative cleavage afforded ester 30, amide 56, and thioester 71, respectively. In the last pathway, acid chloride 80 was reacted with a series of benzylic nucleophiles including 3,4-dimethoxybenzyl alcohol, 3,4-dimethoxybenzyl amine, and 4-methoxy-α-toluene thiol to provide structures of type 82 which were oxidatively cleaved to afford ester 42, amide 31, and thioester 69, respectively.

FIG. 7 shows representative procedures for the solid phase synthesis of ether (75), ester (29), and sulfonate (70) compounds. Additional library members with other types of bridging units were constructed from a phenolic benzopyran system. Initially, resin bound phenol 86 was prepared through the cycloloading of prenylated hydroquinone 85. Library members containing an ether-type bridge were then constructed by alkylation of 86 with 3,4-dimethoxyl benzyl chloride in the presence of $K_2CO_3$ followed by oxidative cleavage to afford ether 75. Ester derivatives were constructed by acylation of phenol 86 with 3,4-dimethoxybenzoic acid, DCC, and 4-DMAP to afford, after oxidative cleavage, ester 29. Lastly, sulfonate derivatives were constructed by treatment of phenol 86 with 3,4-dimethoxybenzenesulfonyl chloride, $Et_3N$, and 4-DMAP followed by oxidative cleavage to afford sulfonate 70. In addition to the representative compounds shown here, this procedure was also repeated in an analogous and parallel manner to prepare compounds 63, 67, 74, and 76 (FIG. 5B).

FIG. 8 gives the procedure for solid phase synthesis of thioamide (72) and thiazole (34) systems. Initially, bromophenol 88 was cycloloaded onto the selenenyl bromide resin to give benzopyran 89. Aryl bromide 89 was subjected to a halogen metal exchange reaction by treatment with n-BuLi at −78° C. and then warming to 0° C. over 2 h at which time 3,4-dimethoxyphenylisothiocyanate was added. Cleavage of the supposed thioamide 90 by treatment with $H_2O_2$ unexpectedly afforded a separable mixture of thioamide 72 and thiazole 34 the latter being presumably formed as a result of excess base present in the halogen-metal exchange reaction.

FIG. 9 is a table giving a summary of biological data from evaluation of the first generation library and proposed lead structures. Results from the study are summarized in the figure.

FIG. 10 is a scheme showing the solution phase synthesis of 3,4,5-trimethoxybenzyl ester (55) and modified pyran analogs and their biological activities. Lead ester 55 was first resynthesized on large scale from 4-hydroxymethyl benzoate 128 by initial O-alkylation with 3-chloro-3-methyl-1-butyne to give ether 129 (Bell, D.; et al. *Synthesis* 1995, 707-712). Heating of alkyne 129 in N,N-diethylaniline at 195° C. for 1 h induced an aromatic Claisen rearrangement to provide benzopyran 130 in quantitative yield (Bell, D.; et al. *Synthesis* 1995, 707-712). The methyl ester of 130 was hydrolyzed (LiOH, THF:$H_2O$, 40° C., 12 h) to the free acid 131 which was coupled to 3,4,5-trimethoxybenzyl alcohol in the presence of DCC and 4-DMAP to furnish ester 55. With the ester 55 in hand, several derivatization reactions were employed to provide the series of pyran-modified analogs 133-140. First, the olefin of ester 55 was dihydroxylated (Fenwick, A. E. *Tetrahedron Lett.* 1993, 34, 1815-1818) (cat $OsO_4$, NMO, t-BuOH:THF:$H_2O$, 25° C., 6 h) to afford diol 133 which was subsequently acetylated to diacetate 134 and reacted with triphosgene to provide carbonate 135. In a second event, ester 55 was treated (Gabbutt, C. D.; et al. *J. Chem. Soc. Perkin Trans. I.* 1994, 1733-1737) with NBS in the presence of $H_2O$ to provide a mixture of bromohydrins 136 and 137 as a result of partial bromination of the terminal aromatic ring (i.e. structure 136). Bromohydrin 137 was subsequently acetylated (AcCl, pyridine, $CH_2Cl_2$, 25° C., 1 h) to afford acetate 138. Additionally, ester 55 was converted to the corresponding epoxide 139 by treatment with m-CPBA (Buckle, D. R.; et al. *J. Med. Chem.* 1990, 33, 3028-3034). Finally, the olefin of ester 55 was saturated by hydrogenation over 10% Pd-C to provide the corresponding saturated pyran system 140.

FIG. 11 is a scheme showing the synthesis of long chain 3,4-dimethoxyphenyl esters. In order to access the relationship between bridge length and biological activity, a set of longer chain analogs 146-148 was synthesized as illustrated in Scheme 6 where alcohols of type 141 were prepared by alkylation of the corresponding bromoalcohols and then coupled to resin-bound acid chloride 80 as previously described.

FIG. 12 is a scheme showing the solution phase synthesis of 3,4,5-trimethoxyphenyl ketone (158) and analogs thereof. Various keto analogs and their derivatives were constructed starting from 4-bromophenol 149. Following the procedure of Ding, 4-bromophenol (149) was alkylated with the in-situ generated trifluoroacetate of 2-methyl-3-butyn-2-ol to afford 150, which was heated to 195° C. in N,N-diethylaniline inducing an aromatic Claisen rearrangement and providing benzopyran 151 in quantitative yield (Ding, C. Z. *Syn. Commun.* 1996, 26, 4267-4273). Subsequent treatment of 151 with n-BuLi afforded aryl lithium 152, which was immediately quenched by addition of aldehyde 155 (synthesized from phenylacetic acid 153, as indicated in Scheme 7) to provide benzyl alcohol 156. Dess-Martin periodinane oxidation of alcohol 156 afforded ketone 158. Incidentally, the methyl ether analog of alcohol 156, compound 157, was also synthesized from alcohol 156 via alkylation with MeI in the presence of NaH. With ketone 158 available, a series of modified keto-analogs were then constructed. Thus, oximes 159-161 were prepared by condensation of ketone 158 with the appropriate hydroxy or alkoxy amines in the presence of $K_2CO_3$. Thioketone 162 was prepared by reaction of ketone 158 with Lawesson's reagent in toluene at 100° C. for 3 h, whereas the corresponding olefin analog 163 was constructed by treatment of ketone 158 with Tebbe reagent. Wolf-Kishner reduction of 158 ($N_2H_4$, KOH, Δ) afforded the alkyl variant 164, while hydrogenation over 10/o Pd-C provided the saturated version (i.e. 165) of ketone 158 as well as of analogs 163 and 164 (i.e. 167 and 166, respectively).

FIG. 13 shows the solution phase synthesis of difluoro- and dichlorostyrene analogues 168 and 169. Several halogenated derivatives of styrene 163 were also prepared. Ketone 165 was treated with $Ph_3P$ in $CCl_4$ at 60° C. to afford dichloroanalog 168 (Clement, B. A.; Soulen, R. L. *J. Org. Chem.* 1974, 39, 97-98). Additionally, ketone 165 was added to a solution of diethyl(difluoromethyl)phosphonate and t-BuLi in DME at −78° C. and then warmed to 25° C., and finally to 85° C. to ultimately afford difluoro-analog 169 (Piettre, S. R.; Cabanas, L. *Tetrahedron Lett.* 1996, 37, 5881-5884)

FIG. 14 shows the solution phase synthesis of 3,4,5-trimethoxyphenylthioether 178 and 3,4,5-trimethoxyphenylsulfone 179. The thioether variant of analog 75 was prepared from 4-mercaptophenol (175) by selective S-alkylation with 3,4,5-tri-methoxy-benzyl chloride and $K_2CO_3$ to provide thioether 176 (Sato, M.; et al. *Eur. J. Med. Chem.* 1995, 30, 403-414). Subsequent O-alkylation was effected with 3-chloro-3-methyl-1-butyne to give alkynyl ether 177. Heating of alkyne 177 in N,N-diethylaniline at 195° C. for 1 h induced an aromatic Claisen rearrangement furnishing benzopyran 178 in quantitative yield. A portion of thioether 178 was then oxidized with OXONE® to afford the corresponding sulfone 179.

FIG. 15 is a graphical summary of structure activity trends observed for benzopyran-based inhibitors of NADH: ubiquinone oxidoreductase. SAR optimization was carried out on each of the four regions (I-IV) of interest guided by the inhibitory potency for NADH:ubiquinone oxidoreductase activity in vitro using bovine heart electron transport particles (see Singer (Singer, T.P. (1974). In *Methods of Biochemical Analysis* (Glick, D. ed., Wiley New York), 22, pp. 123-175) for details).

Figure 16:
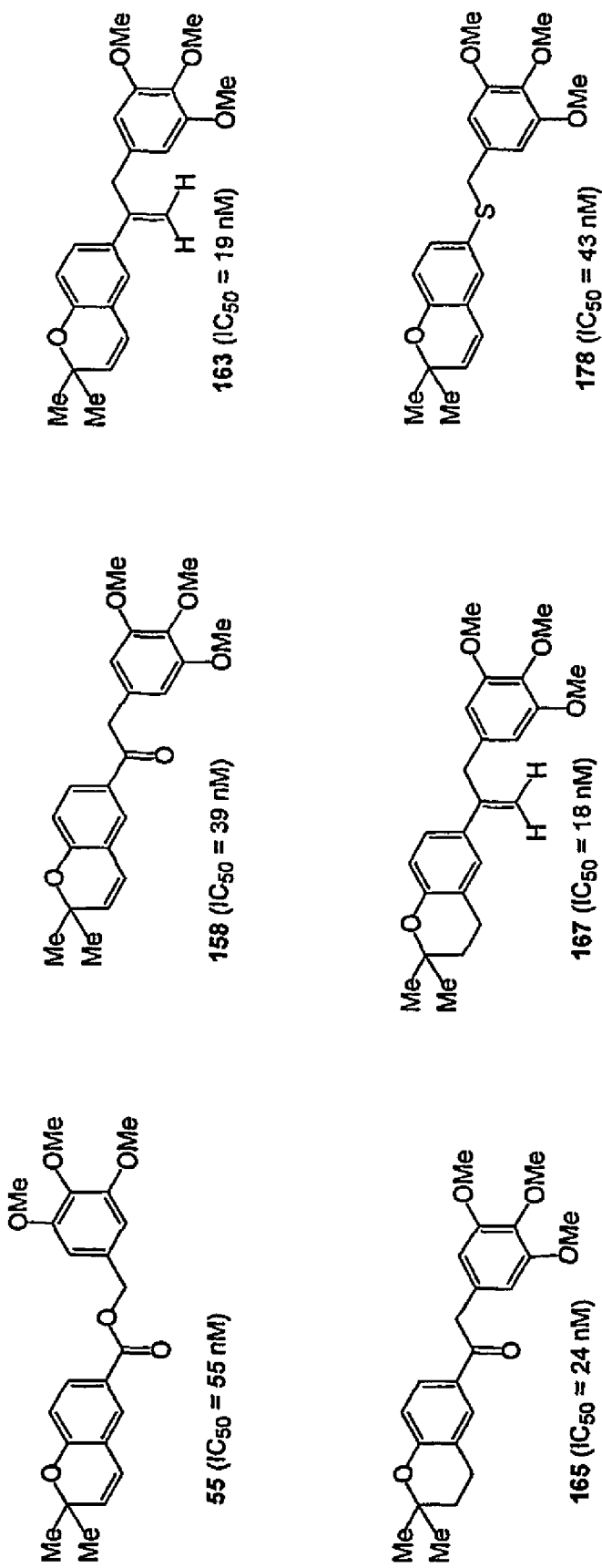
FIG. 16 gives the structures of lead compounds selected for evaluation in cell-based assays. The $IC_{50}$ values are given in parentheses.

FIG. 16 gives the structures of lead compounds selected for evaluation in cell-based assays. The $IC_{50}$ values are given in parentheses. Despite their structural simplicity, the inhibitory activity of these compounds approached that for the most potent natural product in this series, namely deguelin (7, FIG. 3) with an $IC_{50}$ value of 6.9 nM. Moreover, unlike the structurally-complex deguelin, these lead compounds were simple to construct and thus could be readily modified to improve pharmacological properties, solubility or biostability.

FIG. 17 is a table of selected data for growth inhibition ($GI_{50}$) of compounds 55, 158, 165, and 178 in NCI cancer cell lines. Compounds 55, 158, 165 and 178 were also evaluated in the NCI 60-cell cancer panel for the concentration leading to 50% growth inhibition (Monks, A.; et al. *J. Natl. Cancer Inst* 1991, 83, 757-766). Moderate to good activity was observed in growth inhibition in various cell lines. The leukemia cells are generally the most sensitive ($GI_{50}$ from 750 to 2850 nM) and the CNS cells the least sensitive ($GI_{50}$ from 4380 to 12900 nM) to these compounds and the overall potency order is 165>178>158>55. The combination of rather potent growth inhibition and possibly low cytotoxicity makes these compounds interesting lead structures as potential chemopreventive/chemotherapeutic agents.

What is claimed is:

1. A compound represented by the following structure:

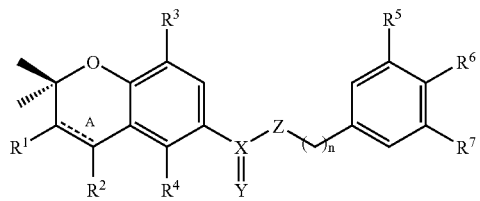

wherein:
A is a π-bond that is either present or absent;
$R^1$ and $R^2$ are radicals independently selected from the group consisting of —H, —F, —Cl, and —Br;
$R^3$ and $R^4$ are —H;
$R^5$, $R^6$ and $R^7$ are radicals independently selected from the group consisting of —H, —OMe, —F, —Cl, and —Br;
Z is —(CH2)—;
X is carbon;
Y is a diradical or pair of radicals selected from the group consisting of =O, =S, =CH$_2$, =CF$_2$, =NOH, =NOMe, and =NOBn; and
n is 0.

2. A compound according to claim 1 possessing the following structure:

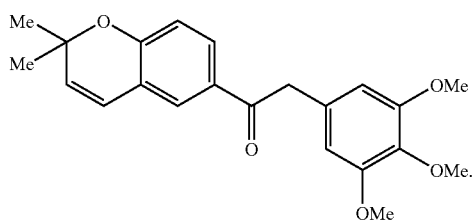

3. A compound according to claim 1 possessing the following structure:

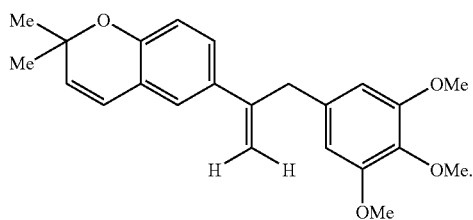

4. A compound according to claim 1 possessing the following structure:

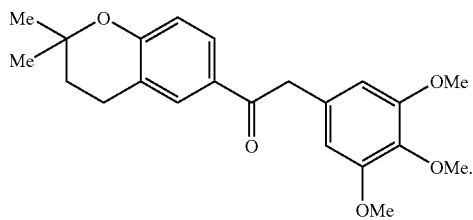

5. A compound possessing the following structure:

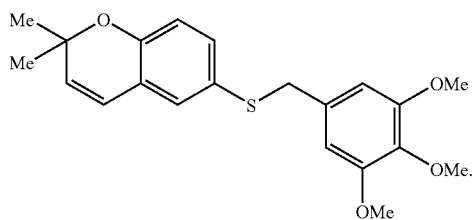

6. A compound according to claim 1 possessing the following structure:

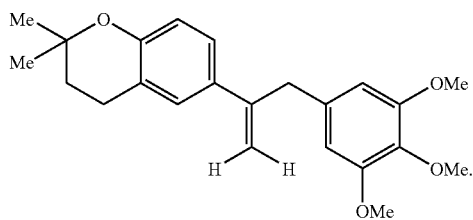

7. A process for inhibiting the growth of a cancer cell in vitro, the process comprising the step of contacting said cancer cell with a concentration of a compound selected from claims 1 or 6 sufficient to inhibit the growth of said cancer cell.

* * * * *

UNITED STATES PATENT AND TRADEMARK OFFICE
CERTIFICATE OF CORRECTION

PATENT NO. : 7,410,998 B2  
APPLICATION NO. : 10/363181  
DATED : August 12, 2008  
INVENTOR(S) : Kyriacos C. Nicolaou et al.

Page 1 of 1

It is certified that error appears in the above-identified patent and that said Letters Patent is hereby corrected as shown below:

In The Specification

Column 1, lines 3-4 insert

--This invention was made with government support under CA046446 and CA086363 awarded by the National Institutes of Health. The government has certain rights in the invention.--

Signed and Sealed this
Twenty-sixth Day of April, 2016

Michelle K. Lee
*Director of the United States Patent and Trademark Office*